US008545893B2

(12) United States Patent
Van Dyke et al.

(10) Patent No.: US 8,545,893 B2
(45) Date of Patent: Oct. 1, 2013

(54) KERATIN BIOMATERIALS FOR TREATMENT OF ISCHEMIA

(75) Inventors: Mark E. Van Dyke, Winston-Salem, NC (US); Thomas L. Smith, Winston-Salem, NC (US); Michael Callahan, Winston-Salem, NC (US); Luke Burnett, Winston-Salem, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 173 days.

(21) Appl. No.: 13/043,062

(22) Filed: Mar. 8, 2011

(65) Prior Publication Data

US 2011/0217285 A1 Sep. 8, 2011

Related U.S. Application Data

(60) Provisional application No. 61/311,574, filed on Mar. 8, 2010.

(51) Int. Cl.
*A61K 35/36* (2006.01)

(52) U.S. Cl.
USPC ........................................ 424/543; 514/21.92

(58) Field of Classification Search
None
See application file for complete search history.

(56) References Cited

U.S. PATENT DOCUMENTS

| 922,692 A | 5/1909 | Goldsmith |
| 926,999 A | 7/1909 | Neuberg |
| 960,914 A | 6/1910 | Heinemann |
| 1,214,299 A | 1/1917 | Grosvenor et al. |
| 2,434,688 A | 1/1948 | Evans |
| 2,445,028 A | 7/1948 | Jones et al. |
| 2,517,572 A | 8/1950 | Jones et al. |
| 2,814,851 A | 12/1957 | Hervey |
| 3,033,755 A | 5/1962 | Jacobi |
| 3,642,498 A | 2/1972 | Anker |
| 3,655,416 A | 4/1972 | Vinson et al. |
| 4,178,361 A | 12/1979 | Cohen et al. |
| 4,357,274 A | 11/1982 | Werner et al. |
| 4,423,032 A | 12/1983 | Abe et al. |
| 4,495,173 A | 1/1985 | Matsunaga et al. |
| 4,570,629 A | 2/1986 | Widra |
| 4,751,074 A | 6/1988 | Matsunaga et al. |
| 4,895,722 A | 1/1990 | Abe et al. |
| 4,959,213 A | 9/1990 | Brod et al. |
| 5,047,249 A | 9/1991 | Rothman et al. |
| 5,300,285 A | 4/1994 | Halloran et al. |
| 5,320,796 A | 6/1994 | Harashima et al. |
| 5,358,935 A | 10/1994 | Smith et al. |
| 5,634,945 A | 6/1997 | Pernia et al. |
| 5,679,819 A | 10/1997 | Jones et al. |
| 5,763,583 A | 6/1998 | Arai et al. |
| 5,932,552 A | 8/1999 | Blanchard et al. |
| 5,948,432 A | 9/1999 | Timmons et al. |
| 6,110,487 A | 8/2000 | Timmons et al. |
| 6,124,265 A | 9/2000 | Timmons et al. |
| 6,159,495 A | 12/2000 | Timmons et al. |
| 6,159,496 A | 12/2000 | Blanchard et al. |
| 6,165,496 A | 12/2000 | Timmons et al. |
| 6,268,454 B1 | 7/2001 | Song et al. |
| 6,270,791 B1 | 8/2001 | Van Dyke et al. |
| 6,270,793 B1 | 8/2001 | Van Dyke et al. |
| 6,274,155 B1 | 8/2001 | Van Dyke et al. |
| 6,274,163 B1 | 8/2001 | Blanchard et al. |
| 6,316,598 B1 | 11/2001 | Van Dyke et al. |
| 6,371,984 B1 | 4/2002 | Van Dyke et al. |
| 6,379,690 B2 | 4/2002 | Blanchard et al. |
| 6,432,435 B1 | 8/2002 | Timmons et al. |
| 6,461,628 B1 | 10/2002 | Blanchard et al. |
| 6,544,548 B1 | 4/2003 | Siller-Jackson et al. |
| 6,808,927 B2 | 10/2004 | Greenfield et al. |
| 6,858,383 B2 * | 2/2005 | Sabbadini ........................ 506/9 |
| 2006/0051732 A1 | 3/2006 | Van Dyke |
| 2009/0017031 A1 | 1/2009 | Fung |

FOREIGN PATENT DOCUMENTS

| DE | 184915 | 12/1905 |
| DE | 22643 | 10/1907 |
| EP | 0468797 A2 | 1/1992 |
| EP | 0 540 357 A2 | 5/1993 |
| GB | 531446 A | 1/1941 |
| GB | 2 241 253 A | 8/1991 |
| JP | 52-148581 A | 12/1977 |
| JP | 53-016091 A | 2/1978 |
| JP | 54-137064 A | 10/1979 |
| JP | 55-051095 A | 4/1980 |
| JP | 56-030909 A | 3/1981 |
| JP | Sho 55-98256 | 2/1982 |
| JP | S57-109797 | 7/1982 |
| JP | 1-174528 | 7/1989 |
| JP | 2-051533 A | 2/1990 |
| JP | 3-011099 A | 1/1991 |
| JP | 4-082561 A | 3/1992 |
| JP | 4-091138 A | 3/1992 |
| JP | Hei 4-189833 | 7/1992 |
| JP | 5-285374 A | 11/1993 |
| JP | 5-285375 A | 11/1993 |
| JP | 5-320358 A | 12/1993 |
| JP | 6-100600 A | 4/1994 |
| JP | 6-116300 A | 4/1994 |
| JP | 6-336499 A | 12/1994 |
| JP | 9-227565 A | 9/1997 |

(Continued)

OTHER PUBLICATIONS

Alexander, P.; Earland, C.; "Structure of wool fibers—Isolation of an α and β-protein in wool." Nature; vol. 166, 1950.

(Continued)

*Primary Examiner* — Allison Ford

(74) *Attorney, Agent, or Firm* — Myers Bigel Sibley & Sajovec, P.A.

(57) ABSTRACT

Provided herein are keratin compositions useful for treating ischemia and/or reperfusion injury, such as that associated with myocardial infarct, ischemic stroke, brain trauma such as traumatic brain injury, hypothermia, chronic wounds, and burns.

28 Claims, 1 Drawing Sheet

(56) References Cited

FOREIGN PATENT DOCUMENTS

| JP | 10-291998 A | 11/1998 |
|---|---|---|
| JP | 10-291999 A | 11/1998 |
| JP | 10-337466 | 12/1998 |
| JP | 2000-191792 A | 7/2000 |
| JP | 2001-087754 A | 4/2001 |
| JP | 2001-114647 A | 4/2001 |
| NL | 51000577 | 12/1941 |
| RU | 2 106 154 C1 | 3/1998 |
| RU | 2 108 079 C1 | 4/1998 |
| WO | WO 91-02538 A1 | 3/1991 |
| WO | WO 93/10827 A1 | 6/1993 |
| WO | WO 93/12819 A1 | 7/1993 |
| WO | WO 98/08550 A1 | 3/1998 |
| WO | WO 99/26570 A1 | 6/1999 |
| WO | WO 99/26595 A1 | 6/1999 |
| WO | WO 99/51175 A1 | 10/1999 |
| WO | WO 00/76437 A1 | 12/2000 |
| WO | WO 01/19283 A2 | 3/2001 |
| WO | WO 01/19305 A1 | 3/2001 |
| WO | WO 01/64033 A2 | 9/2001 |
| WO | WO 02/45508 A1 | 6/2002 |
| WO | WO 03/011894 A1 | 2/2003 |
| WO | WO 03/064449 A2 | 8/2003 |
| WO | WO 03/086491 A2 | 10/2003 |

OTHER PUBLICATIONS

Almog, J.; et al; "Reversible binding of dioxygen to mesoporphyrin IX derivatives at low temperatures."; Journal of the American Chemical Society; vol. 96(17), 1974, pp. 5600-5501.

Almog, J.; et al; "Reversible oxygenation and autoxidation of a capped porphyrin iron (II) complex."; Journal of the American Chemical Society; vol. 97(1), 1975, pp. 227-228.

Amiya, T.; et al; "Conformational studies of the α-helical proteins from wool keratins by c.d." International Journal of Biological Macromolecules; vol. 4, 1982, pp. 165-172.

Ando, H. ; et al; "Separation and characterization of keratin components of merino wool. III: Removal of cuticle by ultrasonic irradiation." Bulletin of the Institute for Chemical Research, Kyoto University; vol. 31, No. 3, 1975, pp. 81-85.

Ashkenasy, G.; et al; "Assemblies of "hinged" iron-porphyrins as potential oxygen sensors."; Journal of the American Chemical Society; vol. 122, No. 6, 2000, pp. 1116-1122.

Baldwin, J.E.; et al; "Binding of dioxygen to iron (II), Reversible behavior in solution."; Journal of the American Chemical Society; vol. 95 (17), 1973, pp. 5757-5759.

Barr, M.; "Oxidation, reduction and hydroysis of wool keratin."; Iowa State Coll. Journal of Science, vol. 12, 1937, pp. 106-107.

Bawden, C.S.; et al; "Expression of bacterial cysteine biosynthesis genes in transgenic mice and sheep: toward a new in vivo acid biosynthesis pathway and improved wool growth." Transgenic Research; vol. 4,1995, pp. 87-104.

Bawden, C.S.; et al; "Expression of wool intermediate filament keratin transgene in sheep fibre alters structure."; Transgenic Research; vol. 7, 1998, pp. 273-287.

Bawden, C.S.; et al; "Improvement of wool quality by transgenesis."; Science Update, Conf: OECD, 2001, pp. 67-76.

Bawden, C.S.; et al; "Sheep transgenesis with keratin and non-keratin genes: expression in the wool follicle for the modified fibre properties and growth rates."; Experimental Dermatology; vol. 8, 1999, pp. 342-343.

Berse, B.; et al.; "Vascular permeability factor (Vascular endothelial growth factor) gene is expressed differentially in normal tissues, macrophages, and tumors." Molecular Biology of the Cell; vol. 3, 1992, pp. 211-220.

Besse, D.; et al; "Synthesis of selenocysteine peptides and their oxidation to diselenide-bridged compounds."; Journal of Peptide Science; vol. 3 (6), 1997, pp. 442-453.

Bettex-Galland, M. et al.; "Advances in Protein Chemistry." Academic Press, vol. 20, 1965.

Bhatnagar, G.M. et al; "Difference sprectra of kerateine-B."; *International Journal of Protein Research*; vol. 1 No. 3, 1969, pp. 213-219.

Bhatnagar, G.M.; et al; "Assessment of confirmational changes in low-sulfur S-(carboxymethyl)keratin from wool."; Australian Journal of Biological Sciences; vol. 20, No. 4, 1967, pp. 827-836.

Bhatnagar, G.M.; et al; "The conformation of the high sulphur proteins of wool. I The preparation and properties of a water soluble metakeratin."; International Journal of Protein Research; vol. 1 (3), 1969, pp. 199-212.

Bhatnagar, G.M.; et al; "The conformation of the high-sulphur proteins of wool. II—Difference spectra of kerateine-B." International Journal of Protein Research I; 1969, pp. 213-219.

Blagrove, R.J.; Frenkel, M.J.; Gillespie, J.M.; "The electrophoresis of the high-tyrosine proteins of keratins on cellulose acetate strips."; Comparative Biochemistry Physiologoly; vol. 50B, 1975, pp. 571-572.

Blessing, M.; et al.; "Transgenic mice as a model to study the role of TGF-β-related molecules in hair follicles." Genes and Development; vol. 7, 1993, pp. 204-215.

Bradbury, J.H.; "The structure and chemistry of keratin fibers." Advanced Protein Chemistry; vol. 27, 1973, pp. 111-211.

Bradbury, J.H.; et al.; "Advances in Protein Chemistry." vol. 27, 1973, pp. 222-375.

Bradbury, J.H.; et al; "Observations by light and electron microscopy on wool cuticle fractions obtained by ultrasonics."; Textile Research Journal; vol. 33, No. 4, 1963, pp. 251-257.

Bradbury, J.H.; et al; "Separation of chemically unmodified histological components of keratin fibers and analyses of cuticles."; Nature; vol. 210, No. 5043, 1966, pp. 1333-1334.

Breinl, F.; et al; "The oxidative breaking up of keratin through treatment with hydrogen peroxide." Z.Physiol. Chemistry; vol. 52, 1907, pp. 158-169.

Broad, A.; Gillespie, J.M., Reis, P.J.; "The influence of sulphur-containing amino acids on the biosynthesis of high-sulphur wool proteins." Australian Journal of Biological Sciences; vol. 23, 1970, pp. 149-164.

Brown, L.F.; et al.; "Expression of vascular permeability factor (Vascular Endothelial Growth Factor) by epidermal keratinocytes during wound healing."; Journal of Experimental Medicine; vol. 176, 1992, pp. 1375-1379.

Brunner, H.; Brunner, A.; "Fractionation of tyrosine-rich proteins from oxidized wool by ion-exchange chromotography and preparative electrophoresis."; European Journal Biochemistry; vol. 32, 1973, pp. 350-355.

Bryson, W.G.; et al; "The analytical tools of proteomics provide new insights into the expression of the wool genome, keratin chemistry and textile processing."; Wool Tcehnology and Sheep Breeding; vol. 49, No. 4, 2001, pp. 246-260.

Cameron, J.H.; et al; "Nickel (II) and cobalt (II) complexes of potentially quinquedentate macrobicyclic ligands. Reversible binding to dioxygen to a cobalt (II) complex"; Journal of the Chemical Society, Dalton Transactions: Inorganic Chemistry; vol. 3, 1993, pp. 397-402.

Campbell, M.E.; Whiteley, K.J.; Gillespie, J.M.; "Compositional studies of high and low-crimp wools."; Australian Journal of Biological Sciences; vol. 25, 1972, pp. 977-987.

Carey, J.R.; et al; "Design and synthesis of novel metalloproteins through reversible encapsulation of metal complexes by proteins." Abstract of Papers, 222nd ACS National Meeting, 2001.

Chatani, E.; et al; "A film formation technology of wool keratin."; Textile and Fashion; vol. 14(5), 1997, pp. 227-235.

Chatani, E.; et al; "Research on merchandizing technology of wool keratin. Film formation technology of wool keratin."; Owari Textile Research Annual Report No. 93, 1998, pp. 93-101.

Clark, R.A.F. Editor; "The Molecular and Cellular Biology of Wound Repair."; Plenum Press 2nd Edition, 1996, 1988.

Japanese Office Action Corresponding to Japanese Patent Application No. 2008-555408; Dispatch Date: Apr. 24, 2012; 3 pages (Foreign Text Only).

Sizin, T.L.; "The occurance of azelaic acid among the oxidation products of keratin." Z. Physiology Chemistry: vol. 62, 1910, pp. 226-228.

Skerrow, D.; Skerrow, C.J.; Hunter, I.; "Epidermal alpha-keratin is neutral-buffer-soluable and forms intermediate filaments under physiological conditions in vitro."; Biochimica et Biophysica Acta; vol. 915. 1987, pp. 125-131.

Smith, A.L.; et al; "Oxidation of Wool—The Effect of Hydrogen Peroxide," Rayon Textile Monthly; vol. 39, 1936. pp. 39,40.
Smith, A.L.; et al; "Oxidation of Wool: The lead acetate test for hydrogen peroxide bleached wool."Journal of Research of the National Bureau of Standards, vol. 16, 1936, pp. 309-312.
Sparrow, L.G.; et al; "Further resolution of the low sulphur S-carboxymethylkerateine fraction from wool by acrylamide-gel electrophoresis."; Journal of Textile Institute; vol. 63, No. 11, 1972, pp. 619-621.
Starger, J.M.; Brown, W.E.; Goldman, A.E.; Goldman, R.D.; "Biochemical and immunological analysis of rapidly purified 10-nm filaments from baby hamster kidney (BHK-21) cells." The Journal of Cell Biology, vol. 78, 1978, pp. 93-109.
Stary, Z.; "Brominated keratin and oxykeratin."; Z. Physiology Chemistry; vol. 144, 1925, pp. 147-177.
Stary, Z.; "Solubility and digestibility of the degradation products of albumoids." Z. Physiology Chemistry; vol. 136, 1924, pp. 160-172.
Steinert, P.M.; et al; "In vitro studies on the synthesis of guinea pig hair keratin proteins." Biochimica et Biophysica Acta; vol. 312, 1973, pp. 403-412.
Stenn, K.S.; "The molecular and structural biology of hair, Introduction."; Annals of New York Academy of Sciences; vol. 83, 1959, pp. 359-512.
Stenn, K.S.; et al.; "Controls of hair Follicle cycling.."; Physiological Reviews; vol. 81, No. 1, 2001, pp. 449-494.
Stenn, K.S.; et al.; "Hair follicle growth controls." Dermatologic Clinics; vol. 14, No. 4, 1996, pp. 543-558.
Stenn, K.S.; et al.; "Molecules of the cycling hair follicle—a tabulated review." Journal of Dermatalogical Science 7(Suppl.) 1994, pp. 109-124.
Stephenson, N.A.; et al; "Preparation and dioxygen binding properties of a new cobalt (II) complex and the crystal structure of the corresponding copper (II) adduct."; Journal of the Chemical Society, Dalton Transactions: Inorganic Chemistry, 150th Anniv. Celebration issue, 1991, pp. 733-738.
Stokes,G.D.; Dunson, W.A.; "Passage of water and electrolytes through natural and artificial keratin membranes." Desalination; vol. 42, 1982, pp. 321-328.
Struessmann, A.; et al.; "Specific radiolabeling of keratin proteins by amidination."; Journal of Chromatography, vol. 268, 1983, pp. 306-310.
Suzuki, E.; et al; "X-ray diffraction and infrared studies of an α-helical fragment from α-keratin." Journal of Molecular Biology; vol. 73, 1973, pp. 275-278.
Tachibana, A. et al.; "Fabrication of wool keratin sponge scaffolds for long-term cell cultivation." Journal of Biotechnology, vol. 93, 2002 pp. 165-170.
Tanabe, T.; Tachibana, A.; Yamauchi, K.; "Keratins: prospective proteinous biomaterial."; Recent Research Developments in Protein Engineering; vol. 1(Pt.2),2001, pp. 247-259.
Tazawa, T.; et al; "Anti-hair keratin monoclonal antibody (HKN-2)."; The Journal of Dermatology; vol. 12, 1985, pp. 313-317.
Thomas, H.; et al; "Isolation of the microfibrillar proteins of wool in the disulfide form." Melliand Textilberichte; vol. 65, No. 3, 1984, pp. 208-209.
Tsai, A.G.; et al; "High viscocity plasma expanders: volume restitution fluids for lowering the transfusion trigger."; Biorheology, vol. 38 (2-3), 2001, pp. 229-237.
Tsai, A.G.; et al; "The unusual properties of effective blood substitutes."; Keio Journal of Medicine; vol. 51 (1), 2002, pp. 17-20.
Tsuchida, E.; "Oxygen ligation of macromolecule-porphyrin complexes."; Journal of the Chemical Society of Japan; No. 6, 1988, pp. 845-852.
Tsuchida, E.; et al; "Cobalt (II)/poly(ethyleneimine) membrane with oxygen binding ability."; Makromolekulare Chemie; vol. 3 (10), 1982, pp. 693-696.
Tucker, D.J.; et al; "Variations in goat fiber proteins."; Australian Journal of Agriculture Research vol. 40, No. 3, 1989, pp. 675-683.
Ueyama, N.; et al; "A novel method for determining the chelation ability of the cysteine-containing peptides with 3,4-toluenedithiol. Application to .cents .2Fe-2S-ferredoxin model systems."; Bulletin of the Chemical Society of Japan; vol. 60 (1), 1987, pp. 283-287.

Van Neste, D.; "The growth of human hair in nude mice."; Dermatologic Clinics; vol. 14, No. 4, 1996, pp. 609-617.
Vasak, M.; et al; "Metal thiolate clusters in cobalt (II)-metallothionein."; Proceedings of the National Academy of Sciences of the United States of America; vol. 78 (11), 1981, pp. 6709-6713.
Vogeli, G.; et al; "High-Sulfur Protein Gene Expression in a Transgenic Mouse." Annals New York Academy of Sciences; vol. 642, 1991, pp. 21-30.
Ward, K.A.; et al.; "The structure of the wool keratin microfibrillar genes." Proceedings of the Australian Biochemical Society; vol. 15, 1983, pp. 70.
Ward, K.A.; "Changes in wool follicle keratinocyte proteinbiosynthesis mediated by inhibitors of follicle bulb cell-proliferation."; Proceedings of the Australian Biochemical Society; vol. 9, 1976, vol. 9, pp. 57.
Ward, K.A.; "Study of keratin biosynthesis in isolated wool follicle cells." Proceedings of the Australian Biochemical Society; vol. 7, 1974, pp. 93.
Weber, K.; Geisler, N.; "The structural relation between intermediate filament proteins in living cells and the alpha-keratins of sheep wool" the EMBO Jjournal; vol. 1 No. 10, 1982, pp. 1155-1160.
Weiss, R.A.; Guilett, Y.A,G.; Freedberg, I.M.; Farmer, E.R.; Small, E.A.; Weiss, M.M.; Sun, T.T; "The use of monoclonal antibody to keratin in human epidermal disease: Alterations in immunohistochemical staining pattern." vol. 81, No. 3, 1983, pp. 224-230.
Werner, S.; et al.; "Large induction of keratinocyte growth factor expression in the dermis during wound healing." Proceedings of the National Academy of Sciences, USA; vol. 89, 1992, pp. 6896-6900.
Whitbread, L.A.; et al; "Expression of the intermediate filament gene, K15, in the basal cell layers of epithelia and the hair follicle."; Experimental Cell Research; vol. 244, 1998, pp. 448-459.
Widra, A.; "Ascoporogenesis by nannizzia grubyia on a soluble fraction of keratin." Mycopathologia et Mycologia Applicata; vol. 30, No. 2, 1966 pp. 141-144.
Wilson, B. W.; et al,; "Complete sequence of a type-I microfibrillar wool keratin gene."; Gene; vol. 73, No. 1, 1988, pp. 21-31.
Wilson, N.; et al; "The role of BMP-2 and BMP-4 in follicle initiation and the murine hair cycle."; Experimental Dermatology; vol. 8, No. 4, 1999, pp. 367-368.
Wolski, T.; Szumilo, H.; "Studies on the kinetics of dissolving feather keratin in the water-urea system." Acta Alimentaria Polinica; vol. 8, (32) No. 1-2, 1982, pp. 102-108.
Wormell, R. L.; "Regenerated fibers from wool." Brit. Rayon Silk Journal; vol. 26, No. 309, pp. 55, 1950.
Wormell, R.L.; "Regenerated protein fibres from wool and casein"; The Journal of the Textile Institute; vol. 39, 1948, T219-T224.
Wormell, R.L.; "Wool, silk and regenerated protein fibers-chemistry." Rev. Textile Progress; vol. 9, 1957, pp. 51-62.
Wortmann, F.J.; et al.; "A method for isolating the cortex of keratin fibers."; Textile Research Journal; vol. 52, 1982, pp. 479-481.
Yakubovich, T.N.; Teslenko, V.V.; Zub, Y.L; "Carriers of molecular oxygen on the basis of metal complexes incorporated in polyorganosiloxane matrices."; Journal of Inorganic and Organometallic Polymers; vol. 6, No. 1, 1996, pp. 43-49.
Yamamura, T.; et al; "Confirmation control of peptides by metal ions. Coordination confirmation correlation observed in a model for Cys-X-Y-Cys/M2+ in proteins."; Inorganic Chemistry; vol. 36 (21), 1997, pp. 4849-4859.
Yamauchi, K. et al.; "Novel proteinous microcapsules from wool keratins." Colloids and Sudaces, B: Biointerfaces; vol. 9, 1997, pp. 117-119.
Yamauchi, K.; "Dissolution of hair and wool. Keratin polymers." Kobunshi Kako; vol. 4i, No. 1, 1994, pp. 14-19.
Yamauchi, K.; "Perspective in chemistry and applications of keratins." Kobunshi; vol. 50, No. 4, 2001, pp. 240-243.
Yamauchi, K.; "Polymer films fom keratin."; Fragrance Journal; vol. 21 (5), 1993, pp. 62-67.
Yamauchi, K.; "Preparation of stable aqueous solution of keratins, and physicochemical and biochemical properties of films." Polymer Preprints—American Chemical Society, Division of Polymer Chemistry; vol. 39, No. 1, 1998, pp. 357-358.

Yamauchi, K.; et al.; "Cultivation of Mouse L929 Fibroblast Cells on Keratins."; Kobunshi Gakkai Yokoshu (Polymer Preprints), Japan; vol. 44, No. 3,1995, pp. 503.

Yamauchi, K.; et al.; "Preparation of stable aqueous solution of keratins, and physicochemical and biodegradational properties of films." Journal of Biomedical Materials Research; vol. 31, No. 4, 1996, pp. 439-444.

Yamauchi, K.; et al; "Enhanced cell adhesion on RGDS-carrying keratin film."; Material Science & Engineering, C.: Biomimetic and Supermolecular Systems; vol. C23, No. 4, 2003, pp. 467-472.

Yao, X.; et al; "Oxygen carrying porphyrin-protein complexes the effect of iron (II) prophyrin structure on dioxygen binding performance."; Research Communications in Biochemistry and Cell & Molecular Biology; vol. 5 (1&2) 2001, pp. 171-174.

Yoshimizu, H.; et al; "C CP/MAS NMR study of the conformation of stretched or heated low-sulfur keratin protein films." Macromolecules,; vol. 24, 1991, pp. 862-866.

Zackroff, R.V.; Goldman, R.D.; "In vitro assembly of intermediate filaments from baby hamster kidney (BHK-21) cells." Proceedings of the National Academy of Sciences, USA; vol. 76, No. 12, pp. 6226-6230, 1979.

Zahn, H. et al.; "Reactivity of amino acid side chains. 18. Reactions of p-fluoro-m,m'-dinitrodiphenyl sulfone and p,p'-difluro-m,m'-dinitrodiphenyl sulfone with wool keratin and silk fibroin."; Kolloid Zeitschrift fuer Polymere; vol. 5, 1973 pp. 289-298.

Zahn, H. et al.; "Wool as a biological composite structure."; Industrial & Engineering Chemistry Product Research and Development; vol. 19, 1980, pp. 496-501.

Zahn, H.; "Progress report on hair keratin research."; International Journal of Cosmetic Science; vol. 24, 2002, pp. 163-169.

Zahn, H.; "Structure and chemistry of wool fibers." Kolloid-Z; vol. 100, 1942, pp. 283-298.

Zahn, H.; "The role of mohair keratin research." Melliand Textilberichte; vol. 71, 1991, pp. 926-931.

Zahn, H.; "Wool research taking part in comtemporary chemistry and physics."Arbeitsgemeinschaft Forsch. Landes Nordheim-Westfalen; vol. 75, 1957, pp. 47-80.

Zahn, H.G.; et al; "2-Dimensional keratin patterns of human hair including cosmetically treated ones."; Journal of Forensic Science Society; vol. 24, No. 4, 1984, pp. 432.

Zahn,H. et al.; "Wool as a biological compounding material." Schriftenreihe des Deautschen Wollforschungsintitutes; vol. 76, 1978, pp. 18-25.

International Search Report and Written Opinion, PCT/US11/27536, mailed May 10, 2011.

Gillis, J.N.; et al; "Selective retention of oxygen using chromatographic columns containing metal chelate polymers."; Analytical Chemistry; vol. 57(8), 1985, pp. 1572-1577.

Goddard, D.R. et al; "A Study on Keratin."; Journal of Biological Chemistry; vol. 106, 1934, pp. 605-614.

Gough, K.H. et al; "Amino acid sequences of alpha-helical segments from S-carboxymethylkerateine-A. Complete sequence of a type-I segment."; Biochemical Journal; vol. 173 (2), 1978, pp. 373-385.

Green, M.R.; Basketter, D.A.; Couchman, J.R.; Rees, D.A.; "Distribution and number of epidermal growth factor receptors in skin is related to epithelial cell growth.;"Developmental Biology; vol. 100, 1983, pp. 506-512.

Greven, R.; et al.; "Morphological origin of the S-carboxymethyl kerateines of wool."; Textile Research Journal vol. 56; 1986, pp. 523-526.

Grotendorst, G.R.; et al.; "Novel transforming growth factor β response element controls the expression of the connective tissue growth factor gene."; Cell Growth and Differentiation; vol. 7, 1996, pp. 469-480.

Han, C.H.; et al; "Effect of glycerol addition on the structure and properties of soluble wool keratose films."; Journal of the Korean Fiber Society; vol. 37,No. 8, 2000, pp. 442-447.

Hanukoglu, I.; et al.; "The cDNA sequence of a human epidermal keratin: Divergence of the sequence but conservation of structure among intermediate filament proteins." Cell; vol. 31, 1982, pp. 243-252.

Happey, F.; "Polycrystralline structure of wool." Nature; No. 4218, 1950, pp. 397-398.

Happey, F.; Wormell, R. L.; "Regenerated keratin fibers from wool." Journal Textile Inst.; vol. 40, 1949, pp. T855-T869.

Happey, F.; Wormell, R. L.; "Regenerated keratin fibers."; Nature ; vol. 163, 1949, p. 18.

Harding, H.W.J.; et al; "Enzymic conversion of arginine to citrulline in a hair protein precursor."; Proceedings of the Australian Biochemical Society; ; vol. 9, 1976, pp. 18.

Harding, H.W.J.; Rogers, G.E.; "Formation of ε (γ- Glutamyl) lysine cross-link in hair proteins. Investigation of transamidases in hair follicles." The Journal of Biochemistry; vol. 11, No. 15, 1972 pp. 2858-2863.

Hardy, M.H.; "The Secret life of the hair follicle."; Trends in Genetics; vol. 8, No. 2, 1992, pp. 55-60.

Harrap, B.S.; et al; "Soluble derivatives of feather keratin. (I) Isolation, fractionation and amiino acid composition." Biochemistry Journal; vol. 92, 1964, pp. 8-18.

Harris, M.; et al.; "Testing for oxidation damage of wool by alkali solubility." The Textile Manufacturer; vol. 63, 1937, pp. 36,37.

Hewish, D.R.; et al; "In vitro growth and differentiation of epithelial cells derived from postembryonic hair follicles."; Australian Journal of Biological Sciences; vol. 35, No. 1, 1982, pp. 103-109.

Hiroshi, S.; et al; "Differential Thermal Analysis of component proteins from wool." Institute for Chemical Research, Kyoto University, Uji, Kyoto; vol. 38, 1982, pp. 517-522.

Hogg, D.M.; et al; "Amino acid sequences of alpha-helical segments from S-carboxymethylkerateine-A. Tryptic and chymotryptic peptides from a type II segment."; Biochemical Journal; vol. 173(2), 1978, pp. 353-363.

Horn, J.C.; Speakman, P.T.; "Relative molecular masses of reduced wool keratin polypeptides" Biochemistry Society Transcript, vol. 14, 1986, pp. 333, 334.

Hu, J.; et al; "Preparation of stable solution of keratin from human hair and structure and properties of the cast film."; Gaofenzi Cailiao Kexue Yu Gongcheng; vol. 18 (2), 2002, pp. 131-133.

Humphries, M.; "Protein-silicone copolymers."; Cosmetics News; vol. 16, No. 92, 1993, pp. 313-318.

Hynd, P.I.; et al; "Amino acid transport in wool and hair follicles."; Experimental Dermatology; vol. 8, 1999, pp. 325-326.

Hübner, G.; et al.; "Strong induction of activin expression after injury suggests an important role of activin in wound repair."; Developmental Biology; vol. 173, 1996, pp. 490-498.

Igarashi, A.; et al.; "Regulation of connective tissue growth factor gene expression in human skin fibroblasts and during wound repair." Molecular Biology of the Cell; vol. 4, 1993, pp. 637-645.

Ikkai, F.; et al; "Dynamic light scattering and circular dichroism studies on heat-induced gelation of hard-keratin protein aqueous solutions."; Biomacromolecules, vol. 3, No. 3, 2002, pp. 482-487.

Ito, H.; et al; "Biocompatability of denatured keratins from wool."; Kobunshi Ronbunshu; vol. 39(4), 1982, pp. 249-256.

Iwatsuki, K.; Viac, J.; Reano, A; Morera, A; Staquet, M.J.; Thivolet, J.; Monier, J.C.; "Comparative studies on the naturally ocurring antikeratin antibodies in human sera."; The Journal of Investigative Dermatology; vol. 87, No. 2, 1986, pp. 179-184.

Jahoda, C.A.B.; et al.; "Dermal-Epidermal Interactions: Adult Follicle-derived cell populations and hair growth."; Dermatologic Clinics; vol. 14, No. 4 1996, pp. 573-583.

Jenkins, B.J. ; et al; "Isolation and characterization of a sheep cysteine-rich cuticle keratin pseudogene."; DNA Sequence; vol. 3, 1992, pp. 181-184.

Jenkins, B.J. et al; "Differential expression of genes encoding a cysteine-rich keratin in the hair cuticle."; Journal of Investigative Dermatology; vol. 103, 1994, pp. 310-317.

Jezowska-Trezebiatowska, B.; et al; " New cobalt (II) complexes, reversibly binding oxygen in aqueous solution."; Bulletin de l'Academie Polonaise des Sciences, Serie des Sciences Chimiques; vol. 20 (3), 1972, pp. 187-192.

Johnson, P.C.; et al; "Oxidative metabolism and blood flow regulation: The search for the missing link."; Journal of Vascular Research; vol. 37 (1) 2000, pp. 83.

Jones, C.M.; et al.; "Involvement of Bone Morphogenetic Protein-4 (BMP-4) and Vgr-1 in morphogenesis and neurogenesis in the mouse."; Development; vol. 111, 1991, pp. 531-542.

Jones, L.N.; "Studies on Microfibrils from alpha-Keratin."; Biochimica et Biophysica Acta; vol. 446. 1976, pp. 515-524.

Jones, L.N.; et al; "Studies of developing human hair shaft cells in vitro."; Journal of Investigative Dermatology; vol. 90, No. 1, 1988, pp. 58-64.

Jozefowicz, M.; Jozefonvicz, J; "Functional Polymers and Cells"; Biomaterials; vol. 16, No. 4, 1988, pp. 831-870.

Katoh, K.; et al; "Multi-functionalization of fiber made of natural polymer."; Aichi-ken Sangayo Gijutsu Kenkyusho Kenkyu Hokoku; vol. 1, 2002, pp. 174-177.

Katsuumi, K.; Ito, M; Kazama, T.; Sato, Y.; "Two dimensional electrophoretic analysis of human hair keratins, especially hair matrix proteins." Archives of Dermatological Research; vol. 281, 1989, pp. 495-501.

Kawano, Y.; et al; "Film and gel of keratins."; Kagaku to Seibutsu; vol. 13 (5), 1975, pp. 291-292.

Kemp, D.J. et al; "Differentiation of avian keratinocytes. Characterization and relationships of the keratin proteins of adult and embryonic feathers and scales."; Biochemistry; vol. 11, No. 6, 1972, pp. 969-975.

Kemp, D.J.; Rodgers, G.E.; "Immunological and immunofluorescent studies on keratin of the hair follicle."; Journal of Cell Science; vol. 7, 1970, pp. 273-283.

Kikkawa, M.; et al; "Solubilization of keratin. Solubilization of feather keratin by oxidation with performic acid."; Hikaku Kagaku,(Leather Chemistry) vol. 20(3), 1974, pp. 151-162.

Klement, V.; et al; "The use of computer-analysis for the quantification of 2-D electrophoretic hair keratin patterns—a pilot study."; Journal of the Forensic Science Society; vol. 24, No. 4, 1984, pp. 440.

Koga, J. et al.; "FTIR study on structural transformation of keratin films induced by stretching."; Journal of Applied polymer Science; vol. 37, 1989, pp. 2131-2140.

Kothapalli, D.; et al.; "Transforming growth factor β induces anchorage-independent growth of NRK fibroblast via a connective tissue growth factor-dependent signaling pathway." Cell Growth and Differentiation; vol. 8, 1997, pp. 61-68.

Kowalska, K.; et al; "New bacterial peptides isolated from structural proteins (keratin of porcine bristle)."; Peptides; Proceedings of the European Peptide Symposium, 25th, 1998, pp. 792-793.

Kozlowski, H.; et al; "Nickel (II) complexes with sulfhydryl containing pepetides. Potentiometric and spectroscopic studies."; Journal of Inorganic Biochemistry; vol. 29 (3), 1987, pp. 187-197.

Kuczek, E.S.; et al; "Sheep wool (glycine+tyrosine)-rich keratin genes: a family of low sequence homology."; European Journal of Biochemistry; vol. 166, 1987, pp. 79-85.

Kulkarni, V.G.; "Further studies on the microfibrils from wool keratin. Part I: the isolation of microfibrils."; Textile Research Journal; vol. 46, No. 11, 1976, pp. 833-835.

Kurimoto, A.; et al.; "Conjugation of keratin sponge with bioactive substances utilizing free cysteine residues. Conjugation of lysozyme."; Nippon Kagakkai Koen Yokoshu; vol. 7, No. 2, 2001, pp. 818.

Kvedar, J.C.; et al.; "Cytokeratins of the bovine hoof : classification and studies on expression."; Biochimica et Biophysica Acta; vol. 884, 1986, pp. 462-473.

Lambre, C.R.; Alaoui-Slimani, N.; Bignon, J.; "An enzyme immunoassay for the auto-antibodies to keratin in normal human serum and in pleural fluids from patients with various malignant or non-malignant lung diseases."; Journal of Clinical and Laboratory Immunology; vol. 20, 1986, pp. 171-176.

Laplaza, C.E.; et al.; "Helix-loop-helix-peptide as scaffolds for the construction of bridged metal assemblies in proteins: the spectroscopic A– cluster structure in carbon monoxide dehydrogenase."; Journal of the American Chemical Society, vol. 123, (42), 2001, pp. 10255-10264.

Lee, K.Y.; "Characterization of Silk Fibroin/S-carboxymethyl kerateine surfaces: Evaluation of the biocompatibility by contact angle measurement."; Fibers and Polymers; vol. 2, No. 2, 2001, pp. 71-74.

Leeder, J.D.; et al; "Readily extracted proteins from Merino wool."; Textile Research Journal; vol. 52, No. 4, 1982, pp. 245-249.

Lennox, F.G.; "Protein fibers. Chemistry."; Review of Textile Progress Journal; vol. 17, 1967, pp. 81-97.

Lennox, F.G.; et al.; "Photochemical degradation of keratins."; Photochemistry and Photobiology; vol. 9, No. 4, 1969, pp. 359-367.

Leon, N.H.; "The chemical reactivity and modification of keratin fibres." Textile Progress vol. 7, No. 1975, pp. 1-81.

Letter,J.E.; Jordan,R.B.; "Complexing of Nickel(II) by cysteine, tyrosine and related ligands and evidence for zwitterion reactivity." Journal of the American Chemical Society; vol. 9, No. 97, 1975, pp. 2381-2390.

Ley, K.; et al; "Release of cuticle from wool by agitation in solutions of detergents."; Australian Journal of Biological Sciences; vol. 41, No. 2, 1988, pp. 163-176.

Ley, K.F.; et al; "Wool cuticle—new approaches to its production and protein characterization."; Proceedings of the Australian Biochemical Society; vol. 14, 1981, pp. 14.

Li, C-X.; et al; "Purification of natural antikeratin autoantibodies from natural human serum and their effect on human keratinocytes cultured in vivo."; British Journal of Dermatology; vol. 145, No. 5, 2001, pp. 737-748.

Lindley, H. et al.; "High-sulfur protein fractions of keratins."; *Applied Polymers Symposium*; vol. 18, No. 1, 1971, pp. 21-35.

Lindley, H.; et al; "The occurance of the Cys-Cys sequence in keratins."; Journal of Molecular Biology; vol. 30, No. 1, 1967, pp. 63-67.

Lindley, H.; et al; "The preparation and properties of a group of proteins from the high sulphur fraction of wool"; Biochemical Journal; vol. 128, No. 4, 1972, pp. 859-867.

Lindley, H.; et al; "The reactivity of the disulphide bonds of wool"; Biochemical Journal; vol. 139, No. 3, 1974, pp. 515-523.

Lindley H.; et al; "Disulphide interchange reactions involving cyclosystine and their relevance to problems of α-keratin structure" Biochemical Journal; vol. 108, No. 4, 1968, pp. 701-703.

Lissizin, Th.; "Behavior of keratin sulfur and cystin sulfur, in the oxidation of these proteins by potassium permanganate." Biochemistry Bulletin vol. 4, 1915, pp. 18-23.

Lissizin, Th.; "The oxidation products of keratin by oxidation with permanganate." Z. Physiology Chem. vol. 173, 1928, pp. 309-311.

Liu, S.M.; et al; "Transsulfuration, protein synthesis rate and follicle mRNA in the skin of young Merino lambs in response to infusions of methionine and serine."; British Journal of Nutrition; vol. 83, No. 4, 2000, pp. 401-409.

Lotay, S.S.; Speakman, P.T.; "Three-chain merokeratin from wool may be a fragment of the microfibril component macromolecule"; Nature; vol. 265, 1977, pp. 274-277.

Lyons, K.M.; et al.; "Patterns of expression of murine Vgr-1 and BMP-2a RNA suggest that transforming growth factor-β-like genes coordinately regulate aspects of embryonic development." Genes & Development; vol. 3, 1989, pp. 1657-1668.

Mack, J.W.; Torchia, D.A.; Steinert, P.M.; "Solid-State NMR Studies of the Dynamics and Stucture of Mouse Keratin Intermediate Filaments."; Biochemistry; vol. 27, No. 15. 1988, pp. 5418-5426.

MacKinnon, P.J.; et al; "An ultrahigh-sulphur keratin gene of the human hair cuticle is located at 11q13 and cross-hybridizes with sequences at 11p15."; Mammalian Genome; vol. 1, 1991 pp. 53-56.

MacLaren, J.A.; "The extent of reduction of wool proteins by thiols." The Australian Journal of Chemistry; vol. 15,No. 4, 1962, pp. 824-831.

Marikovsky, M.; et al.; "Appearance of heparin-binding EGF-like growth factor in wound fluid as a response to injury."; Proceedings of the National Academy of Sciences, USA; vol. 90, 1993, pp. 3889-3893.

Marshall, R.C. et al; "High-sulfur proteins in mammalian keratins: a possible aid in classification."; Australian Journal of Zoology; vol. 25, No. 1, 1977, pp. 121-132.

Marshall, R.C.; "Successful isoelectric-focusing of wool low-sulphur proteins.";Journal of Chromatography; vol. 172, 1979, pp. 351-356.

Marshall, R.C.; "Analysis of the proteins from single wool fibers by two-dimensional polyacrylamide-gel electrophoresis."; Textile Research Journal; vol. 51, No. 2, 1981, pp. 106-108.

Marshall, R.C.; "Changes in wool low-sulphur and high-sulphur protein-components following chemical defleecing."; Textile Research Journal; vol. 51, No. 6, 1981, pp. 384-388.

Marshall, R.C.; "Characterization of the proteins of human hair and nail by electrophoresis."; Journal of Investigative Dermatology; vol. 80, No. 6, 1983, pp. 519-524.

Marshall, R.C.; "Cysteine-rich proteins of mouse hair."; Proceedings of the Australian Biochemical Society; vol. 8, 1975, pp. 4.

Marshall, R.C.; "Forensic identification of hairs by electrophoresis."; Journal of the Forensic Society; vol. 24, No. 4, 1984, pp. 340.

Marshall, R.C.; "Genetic variation in the proteins of human nail."; Journal of Investigative Dermatology; vol. 75, No. 3, 1980, pp. 264-269.

Marshall, R.C.; et al; "An investigation of the relationship of wool textile properties to fiber protein composition."; Proceedings of the International Wool Textile Research Conf.; vol. 1, 1990, pp. 266-275.

Marshall, R.C.; et al; "Examination of proteins of wool cuticle by two-dimensional gel-electrophoresis."; Textile Research Journal; vol. 56, No. 12, 1986, pp. 772-774.

Crewther, W.G. et al; "Helix-rich fraction from the low-sulphur proteins of wool."; Nature; vol. 207,(4994), 1965, pp. 295.

Crewther, W.G.; Effect of aftertreatment on the stability of set wool fibers. Comments; Journal of the Society of Dyers and Colourist; vol. 86, No. 5, 1970, pp. 208.

Crewther, W.G.; "The concept of internal pH in wool fibers and the interpretation of data relating to setting."; Journal of the Society of Dyers and Colourist; vol. 81, (4), 1965, pp. 156-158.

Crewther, W.G.; "The viscoelasticity of alpha keratin fibers."; Experimental Dermatology; vol. 8 (4), 1999, pp. 343-344.

Crewther, W.G.; "Preparation and properties of large peptides from the helical regiones of the low-sulfur proteins of wool."; Applied Polymer Symposia; vol. 18, No. 1, 1971, pp. 1-20.

Crewther, W.G.; "Structure of .alpha.-keratin."; Textile Research Journal; vol. 42, No. 4, 1972, pp. 251-252.

Crewther, W.G.; "The stress-strain characteristics of animal fibers after reduction and alkylation."; Textile Research Journal; vol. 35, No. 10, 1965, pp. 867-877.

Crewther, W.G.; "Thiol-disulfide interchange reactions in the setting of single wool fibers." Journal of the Society of Dyers and Colourist; vol. 82, No. 1, 1966, pp. 54-58.

Crewther, W.G.; at al; "Effect of S-carboxymethylation of wool proteins on the iodination of tyrosine residues."; Textile Research Journal; vol. 41, No. 3, 1971, 99.267.

Crewther, W.G.; Dowling, L.M.; "The relation between the disulphide content of wool and the two-stage supercontraction of wool fibers in solution of LiBr."; Biochimica et Biophysica Acta; vol. 46, 1961, pp. 605-606.

Crewther, W.G.; et al; "Amino acid sequences of alpha-helical segments from S-carboxymethylkerateine-A. Complete sequence of a type II segment."; Biochemical Journal; vol. 173 (2), 1978, pp. 365-371.

Crewther, W.G.; et al; "Amino acid sequences of α-helical segments from S-carboxymethlykerateine-A. Tryptic and chymotryptic peptides from a type-II segment"; Biochemistry Journal; vol. 173, 1978 pp. 353-363.

Crewther, W.G.; et al; "Formation of various crosslinkages in wool and their effect on the supercontraction properties of the fibers."; Textile Research Journal; vol. 37, No. 9, 1967, pp. 736-745.

Crewther, W.G.; et al; "Low-sulfur proteins from α-keratins. Interrelationship between their amino acid compositions, α-helix contents, and the supercontraction of the parent keratin." Biopolymers, vol. 4, 1966, pp. 905-916.

Crewther, W.G.; et al; "Reduction of S-carboxymethlycysteine and methionine with sodium in liquid ammonia." Biochimica et Biophysica Acta; vol. 164, 1969, pp. 606-609.

Crewther, W.G.; et al; "Structure of intermediate filaments."; International Journal of Biological Macrmolecules; vol. 5, No. 5, 1983, pp. 267-274.

Crewther, W.G.; et al; "The chemistry of keratins."; Advance Protein Chemistry; vol. 20, 1965 pp. 191-346.

Crewther, W.G.; et al; "The preparation and properties of a helix-rich fraction obtained by partial proteolysis of low sulfur S-Carboxymethylkerateine from wool." The Journal of Biological Chemistry; vol. 242, No. 19, 1967, pp. 4310-4319.

Dale, H.N.; "Keratin and other coatings for pills."; Pharmacology Journal; vol. 129, 1932, pp. 494-495.

Damaglou, A.P.; et al; "The hydrolysis by thermolysin of dipeptide derivatives that contain substituted cysteine" Biochemical Journal; vol. 123, No. 3, 1971, pp. 379-384.

Darskus, R.L.; et al.; "Breed and species differences in the hair proteins of four genera of caprini." Australian Journal of Biological Sciences; vol. 24, 1971, pp. 515-524.

Darskus, R.L.; et al; "The possibility of common amino acid sequences in high sulphur protein fractions from wool." Australian Journal of Biological Sciences; vol. 22, 1969, pp. 1197-1204.

De Sanctis, G.; et al; "Mini-myoglobin—Electron paramagnetic resonance and reversible oxygenation of the cobalt derivative."; Journal of Molecular Biology; vol. 222, 1991, pp. 637-643.

Dedeurwaerder, R.A.; et al; "Selective extraction of protein fraction from wool keratin." Nature vol. 203, 1964, pp. 48,49.

Dobb, M.G.; et al; "Electron microscopy of fibrous keratins."; Symposuim of fibrous protein, Int Conf.; 1967, pp. 267-278.

Dowling, L.M.; Crewther, W.G.; Inglis, A.S.; "The primary structure of component 8c-1, a subunit protein of intermediate filaments in wool keratin."; Biochemistry Journal vol. 236, 1986, pp. 695-703.

Dowling, L.M.; Crewther, W.G.; Parry, D.A.D.; "The secondary structure of component 8c-1, of alpha-keratin."; Biochemistry Journal; vol. 236, 1986, pp. 705-712.

Dowling, L.M.; et al; "Effect of the solvent on the iodanation of a tyrosine derivative and its relation to iodination of wool."; Textile Research Journal; vol. 41, No. 1, 1971, pp. 65-69.

Dowling, L.M.; et al; "Isolation of components from the low sulphur proteins of wool by fractional precipitation."; Preparative Biochemistry, vol. 4(3), 1974, pp. 203-226.

Downes, A.M.; et al; "Evaluation of modified [35S] methionine and [35S] casein preparations as supplements for sheep"; British Journal of Nutrition; vol. 24, No. 4, 1970, pp. 1083-1089.

Downes, A.M.; et al; "Matabolic fate of parenterally administered sulphur containing amino acids in sheep and the effects on growth and composition of wool" ; Australian Journal of Biological Sciences; vol. 23, No. 5, 1970, pp. 1077-1088.

Downes, A.M.; Ferguson,K.A,; Gillespie, J.M.; Harrap, B.S.; "A study of the proteins of the wool follicle. " Australian Journal of Biological Science; vol. 19. 1966, pp. 319-333.

Dunn, S.M.; et al; "Regulation of hair gene expression."; Experimental Dermatology, vol. 8, 1999, pp. 341-342.

Earland, C.; et al; "Structure of keratin. II. Amino acid content of fractions isolated from oxidized wool."; Biochimica et Biophysica Acta; vol. 22, 1956, pp. 405-411.

Ebright, Y.W.; et al; "N-(Iodoacetyl)-p-phenylenediamine-EDTA: A regent for high-efficiency incorporation of an EDTA-metal complex at a rationally selected site within a protein."; Bioconjugate Chemistry; vol. 4 (3), 1993, pp. 219-225.

Edwards, B.; et al; "Chemical studies on powdered keratins." Journal of Biological Chemistry; vol. 154, 1944, pp. 593-596.

Elleman, T.C.; et al; Amino acid sequences of alpha-helical segments from S-carboxymethylkerateine-A. Statistical analysis; Biochemical Journal; vol. 173 (2), 1978, pp. 387-391.

Elleman, T.C.; et al; "Periodicity in high sulphur proteins from wool"; Nature; vol. 246, 1973, pp. 530-531.

Elod, E.: et al.; "Reactions of wool fiber and alterations in the fine structure."; Melliand Textillber; vol. 21, 1940, pp. 385-388.

Elod, E.; et2 al.; The nature of the reactivity of wool. Melliand Textilber; vol. 21, 1940, pp. 617-622.

Elod, E; et al; "The structure and reactivity of the woolen fiber. IX. The effect of $H_2O_2$ on wool."; Melliand Textilber; vol. 23, 1942, pp. 313-316.

Elod,E. et al.; "The infiltration of heavy metal sulfides in the keratin fiber." Chem Ber. vol. 74B, 1941, pp. 1759-1762.

Eriksson, A.; et al.; "PDGF α- and β-receptors activate unique and common signal transduction pathaways."; The EMBO Journal; vol. 11, 1992, pp. 543-550.

Filshie, B.K. et al; "The Fine Structure of α - Keratin." Journal of Molecular Biology; vol. 3, 1961, pp. 784-786.

Filshie, B.K.; Rodgers, G.E,; "An electron microscope study of the fine structure of feather keratin."; The Journal of Cell Biology; vol. 13, 1962, pp. 1-12.

Frank, S.; et al.; "Transforming growth factors β1, β2, and β3 and their receptors are differentially regulated during normal and impaired wound healing." The Journal of Biological Chemistry; vol. 271, 1996, pp. 10188-10193.

Frankel, M.J.; Powell, B.C.; Ward, K.A.; Sleigh, M.J., Rodgers, G.E.; "The keratin BIIIB gene family: Isolation of cDNA clones and stucture of a gene and a related pseudogene."; Genomics vol. 4, 1989, pp. 182-191.

Fraser, B.R.D, et al; "Intermediate Filaments in α-keratins." Proceeedings of the National Academy of Sciences, USA.; Biochemistry; vol. 83, 1986, pp. 1179-1183.

Fraser, R.D.B.; et al; "Disulphide bonding in α-keratin."; International Journal of Biological Macromolecules; vol. 10, issue 2, 1988, pp. 106-112.

Fraser, R.D.B.; et al; "Microscopic Observations of the Alkaline-Thioglycollate Extraction of Wool."Short Communications, Wool Textile Research Laboratory; vol. 12, 1953, pp. 484-485.

Fraser, R.D.B.; et al; "Molecular organization in Alpha-Keratin."; Nature; vol. 193, 1962, pp. 1052-1055.

Fraser, R.D.B.; Gillispie, J.M.; "Wool structure and biosysnthesis." Nature vol. 126 1976, pp. 650-654.

Fraser, R.D.B.; Macrae, T.P.; "Helical models of feather keratin structure." Nature; vol. 195, No. 4847, 1962, pp. 1167,1168.

Fraser, R.D.B.; MaCrae, T.P.; Rogers, G.E.; "Structure of Alpha-Keratin." Nature; vol. 183, 1959, pp. 592-594.

Fraser,R.D.B.; Gillespie, J.M.; Macrae,T.P.; "Tyrosine-rich proteins in keratins."; Comparative Biochemistry and Physiology; vol. 44B, 1973, pp. 943-949.

Fratini, A.; et al; "Dietary cysteine regulates the levels of mRNAs encoding a family of cysteine-rich proteins of wool,"; Journal of Investigative Dermatology; vol. 102, 1994, pp. 178-185.

Frenkel, M.J. et al.; "Heterogeneity of tyrosine-rich proteins of wool."; Proceedings of the Australian Biochemical Society; vol. 7, 1974, p. 4.

Frenkel, M.J.; "Alkali susceptible amides in tyrosine-rich proteins of wool."; Proceedings of the Australian Biochemical Society; vol. 10, 1977, p. 21.

Frenkel, M.J.; et al.; "Studies of the ribonucleic-acids coding for the keratin complex of hair."; Proceedings of the Australian Biochemical Society; vol. 12, 1979, pp. 87.

Frenkel, M.J.; et al.; "Factors influencing biosynthesis of tyrosine-rich proteins of wool."; Australian Journal of Biological Sciences; vol. 27, 1974, pp. 31-38.

Frenkel, M.J.; et al; "The keratin BIIIB gene family: isolation of cDNA clones and structure of a gene and a related pseudogene."; Genomics; vol. 4, No. 2, 1989, pp. 182-191.

Frenkel, M.J.; Gillespie, J.M.; Reis, P.J.; "Studies on the inhibition of synthesis of the tyrosine-rich proteins of wool."; Australian Journal of Biological Sciences; vol. 28, 1975, pp. 331-338.

Frenkel, M.J.; Gillespie, J.M.; Woods, E.F.;"The isolation and properties of a tyrosine-rich protein from wool: component 0.62."; European Journal Biochemistry; vol. 34, 1973, pp. 112-119.

Fujisawa, K.; et al; "Synthesis and characterization of zinc family thiolato complexes.";Abstracts, Symposium on Biofunctional Chemistry, vol. 14, 1999, pp. 52-53.

Gillespie, J.M. et al; "Evidence of homology in a high-sulphur protein fraction (SCMK-B2) of wool and hair α-keratins."; Biochemistry Journal; vol. 110, No. 2, 1968, pp. 193-198.

Gillespie, J.M. et al; "A comparative study of high-sulphur proteins from α-karatins." Comparative Biochemistry and Physiology; vol. 15, 1965, pp. 175-185.

Gillespie, J.M.; "Reaction of Sodium Borohydride with wool." Nature; vol. 183 No. 4657, 1959, pp. 322, 323.

Gillespie, J.M.; "Swelling of keratins in formic acid." Textile Research Journal; vol. 40, No. 9, 1970, pp. 853-855.

Gillespie, J.M.; "The isolation and properties of some soluble proteins from wool. (II) the preferential extracation of high-sulphur proteins."; Australian Journal of Biological Sciences; vol. 15, No. 1, 1962, pp. 262-277.

Gillespie, J.M.; "The isolation from wool of a readily extractable protein of low sulphur content." Biochimica et Biophysica Acta; vol. 27, 1958, pp. 225,226.

Gillespie, J.M.; "The probable role and location of high-glycine-tyrosine proteins in the structure of keratins." Biopolymers, vol. 17, 1978, pp. 2743-2745.

Gillespie, J.M.; "The relation between the crimp of wool and its content of high-sulfur proteins."; Textile Research Journal; vol. 35, No. 12, 1965, pp. 1128-1129.

Gillespie, J.M.; "Keratin structure and changes with copper deficiency."; *Australian Journal of Dermatology*; vol. 14, No. 3, 1973, pp. 127-131.

Gillespie, J.M.; Broad, A.; "A further study on the dietary-regulated biosynthesis of high-sulphur wool proteins." Biochemistry Journal; vol. 112, 1969, pp. 41-49.

Gillespie, J.M.; Darskus, R.L.; "Relation between the tyrosine content of various wools and their content of a class of protiens rich in tyrosine and glycine."; Australian Journal Biological Science; vol. 24, 1971, pp. 1189-1197.

Gillespie, J.M.; et al.; "Changes in the matrix proteins of wool and mouse hair following the administration of depilatory compounds." Australian Journal of Biological Sciences; vol. 33, 1980, pp. 125-136.

Gillespie, J.M.; et al.; "Proteins of the hard keratins of Echidna, Hedgehog, Rabbit, Ox and Man."; Australian Journal of Biological Sciences, vol. 30, 1977, pp. 401-409.

Gillespie, J.M.; et al; "The Diversity of Keratins"; Comparative Biochemistry and Physiology; vol. 47, No. 2,1974, pp. 339-346.

Gillespie, J.M.; et al; "Variable composition of hair and high-sulfur proteins in trichothiodystrophy."; Journal of Applied Cosmetology; vol. 7, No. 2, 1989, pp. 39-48.

Gillespie, J.M.; Frenkel, M.J.; "The macroheterogeneity of type I tyrosine-rich proteins of merino wool."; Australian Journal Biological Science; vol. 27, 1974, pp. 617-627.

Gillespie, J.M.; Inglis, A.S.; "High-sulphur proteins as a major cause of variation in sulphur content between α-keratins." Nature; vol. 207, 1965, pp. 1293,1294.

Gillespie, J.M.; Marshall, R.C.; "A comparision of the proteins of normal and trichothiodystrophic human hair." The Journal of Investigative Dermatology; vol. 80, 1983, pp. 195-202.

Gillespie, J.M.; Marshall, R.C.; Moore, G.P.; Panaretto, B.A.; Robertson, D.M.; "Changes in the proteins of wool following treatment of sheep with epidermal growth factor."; The Journal of Investigative Dermatology; vol. 79, No. 3, 1982, pp. 197-200.

Gillespie, J.M.; Reis, P.J.; "The dietary regulated biosynthesis of high-sulphur wool proteins."; Biochemistry Journal; vol. 98, 1966, pp. 669-677.

Gillespie, J.M.; Simmonds, D.H.; "Amino acid composition of a sulphur-rich protein from wool."; Biochimica et Biophysica Acta; vol. 39, 1960, pp. 538-539.

Gillespie,J.M.; "Proteins rich in glycine and tyrosine from keratins."; Comparative Biochemistry and Physiology ; vol. 41B, 1972, pp. 723-734.

Marshall, R.C.; et al; "High sulphur proteins and α-keratins II.* Isolatioin and partial characterization of purified components from mouse hair."; Australian Journal of Biological Sciences.; vol. 29, 1976, pp. 11-20.

Marshall, R.C.; et al; "High sulphur proteins from α-keratins I. Heterogeneity of the proteins from mouse hair."; Australian Journal of Biological Sciences; vol. 29, 1976, pp. 1-10.

Marshall, R.C.; et al; "Possible identification of specialty fibers y electrophoresis."; Textile Research Journal; vol. 54, No. 2, 1984, pp. 126-128.

Marshall, R.C.; et al; "Protein changes after short thermal treatments of wool fibrics."; Textile Research Journal; vol. 53, No. 12, 1983, pp. 792-794.

Marshall, R.C.; et al; "Sequence studies of wool proteins rich in glycine and aromatic residues."; Proceedings of the Australian Biochemical Society; vol. 12, 1979, pp. 12.

Marshall, R.C.; Gillespie, J.M.; "The keratin proteins of wool, horn and hoof from sheep." Australian Journal of Biological Sciences; vol. 30, 1977, pp. 389-400.

Marshall, R.C; et al.; "Heterogeneity and incomplete disulfide reduction in the high sulphur proteins of wool." Australian Journal of Biological Sciences; vol. 31, 1978, pp. 219-229.

Martin, P. "Wound Healing-Aiming for Perfect Skin Regeneration."; Science; vol. 276, 1997, pp. 75-81.

Mason, E.D.; et al.; "Dorsal midline fate in *Drosophila* embryos requires twisted gastrulation, a gene encoding a secreted protein related to human connective tissue growth factor." Genes and Development vol. 8, 1994, pp. 1489-1501.

Matsunaga, A.; et al; "Studies on the chemical property of human hair keratin. Part I. Fractionation and amino acid composition of human hair keratin solubilized by performic acid oxidation."; Hikaku Kagaku; vol. 27(1), 1981, pp. 21-29.

Mazzoni, M.C.; et al; "Blood and plasma viscocity and microvascular function in hemodilution. A perspective from LaJolla, California."; European Surgical Research; vol. 34, (1-2), 2002 Ref. 35.

McCloghry, C.E.; et al; "Wool follicles initiate, develop and produce fibres in ovine foetal skin grafts."; Proceedings of the Australian Society of Animal Production; vol. 18, 1990, pp. 518.

McMillin, D.R.; Holwerda, R.A.; Gray, H.B.; "Preparation and spectroscopic studies of cobalt (II) stellacyanin"; Proceedings of the National Academy of Sciences; vol. 71, No. 4, 1974, pp. 1339-1341.

McMillin, D.R.; Rosenberg, R.C.; Gray, H.B.; "Preparation and spectroscopic studies of cobalt (II) derivatives of blue copper proteins."; Proceedings of the National Academy of Sciences; vol. 71, No. 12, 1974, pp. 4760-4762.

Mies, H.H.; et al.; "Preparation of soluble proteins from wool."; Leder; vol. 39, 1988, pp. 1-9.

Mies, H.H.; Zahn, H.; "Chromatographic and electrophoretic investigations of the properties of unprotected low-sulphur wool keratins."; Journal of Chromatography; vol. 405, 1987, pp. 365-370.

Mitsui, S.; Ohuchi, A; Hotta, M.; Tsuboi, R.; Ogawa, H.; "Genes for a range of growth factors and cyclin-dependent kinase inhibitors are expressed by isolated human hair follicles." British Journal of Dermatology; vol. 137, 1997, pp. 693-698.

Miwa, M.; et al; "Effects of fiber length on the tensile strength of epoxy/glass fiber and polyester/glass fiber composites." Journal of Applied Polymer Science; vol. 25, 1980, pp. 795-807.

Miyamoto, T.: et al; "Sorption Behavior of Heavy Metal Ions on S-Subtituted Kerateine Gels." Institute for Chemical Research; vol. 34, No. 10, 1978, pp. T-447-T-454.

Moll, R.; et al.; "The catalog of humans cytokeratins: Patterns of expression in normal epithelia, tumors and cultured cells." Cell; vol. 31, 1982, pp. 11-24.

Mueller, R.V.; et al.; "The effect of insulinlike growth factor I on wound healing variables and macrophages in rats." Archives of Surgery; vol. 129, 1994, pp. 262-265.

Nakamura, A.; et al; "Cysteine-containing oligopepetide model complexes of iron-sulfur proteins."; Advances in Inorganic Chemistry; vol. 33, 1989, pp. 39-67.

Nakamura, Y.; et al; "Cystine in wool. Relation between sulfhydryl group and supercontraction." Sen-i Gakkaishi, vol. 16, 1960, pp. 852-858.

Nancarrow, M.J. et al: "Expression of ornithine decarboxylase during embryonic development of wool follicles."; Experimental Dermatology; vol. 8, 1999, pp. 362-368.

Noishiki, Y.; et al; "Application of denatured wool keratin derivatives to an antithrombogenic biomaterial. Vascular graft coated with a heparinized keratin derivative."; Kobunshi Ronbunshu; vol. 39(4), 1982, pp. 221-227.

Norman, J.A.T.; et al; "Reversible complexes for the recovery of dioxygen."; Procedings of the Annual IUCCP Symposium; 1987, pp. 107-125.

Okamoto, S.; "Formation of films from some proteins."; Nippon Shokuhin Kogyo Gakkaishi; vol. 24(1), 1977, pp. 40-50.

O'Shea, J.M.; et al; "The effect of ultrasonic irradiation on proteins." Australian Journal of Biological Sciences; vol. 26, 1973, pp. 583-590.

Osterberg, R.; "Metal complexes of peptides."; Metal Catalog Lipid Oxidation; Sv. Inst. Konserveringsforsk, Symposium, Goteberg Sweden, 1967, pp. 119-127.

Panteleyev, A.A.; et al.; "Hair follicle predetermination."; Journal of Cell Science; vol. 114, 2001, pp. 3419-3431.

Parry, D.A.D.; et al; "Fibrous proteins: Scientific, Industrial and Medical aspects."; An Academic Press Fast Publication; vol. 1, 1979, pp. 1-132.

Parry, D.A.D.; et al; "Structure of α-keratin: Structural implication of the amino acid sequences of the type I and type II chain segments."; Journal of Molecular Biology; vol. 113, 1977, pp. 449-454.

Pauling, L.; Corey, R.B.; "The structure of feather rachis keratin." Proceedings of the National Academy of Sciences; vol. 37,No. 5, 1951, pp. 256-261.

Pauling, L.; Corey, R.B.; "The structure of hair, muscle, and related proteins."; Proceedings of the National Academy of Sciences; vol. 37, No. 5, 1951, pp. 261-271.

Peters, L.; "Affinity of ions for keratin."; Journal of Textile Institute; vol. 58, No. 4, 1967, pp. 179-180.

Peus, D., et al.; "Growth factors in hair organ development and the hair growth cycle." Dermatologic Clinins; vol. 14, No. 4, 1996, pp. 559-572.

Philpott, M.P.; et al.; "Whole hair follicle culture." Dermatologic Clinics; vol. 14, No. 4, 1996, pp. 595-607.

Powell, B.C.; "The keratin proteins and genes of wool and hair."; Wool Technology and Sheep Breeding; vol. 44, No. 2, 1996, pp. 100-118.

Powell, B.C.; et al; "The Notch signalling pathway in hair growth."; Mechanisms of Development; vol. 78, 1988, pp. 189-192.

Powell, B.C.; et al; "Characterization of a gene encoding a cysteine-rich keratin associated protein synthesized late in rabbit hair follicle differentiation."; Differentiation; vol. 58, 1995, pp. 227-232.

Powell, B.C.; et al; "Characterization of hair (wool) keratin intermediate filament gene domain."; Journal of Investigative Dermatology; vol. 102, 1994, pp. 171-177.

Powell, B.C.; et al; "Mammalian keratin gene families: organization of genes coding for the B2 high sulphur proteins of sheep wool."; Nucleic Acids Research; vol. 11, 1983, pp. 5327-5346.

Powell, B.C.; et al; "Regulation of Keratin Gene Expression in Hair Follicle Differentiation." Annals New York Academy of Sciences; vol. 642, 1991, pp. 1-20.

Powell, B.C.; et al; "The role of keratin proteins and their genes in the growth, structure and properties of hair"; EXS; vol. 78, 1997, pp. 59-148 Ref: 284.

Powell, B.C.; et al; "Transgenic sheep and wool growth: possibilities and current status."; Reproduction, Fertility, and Development; vol. 6, 1994, pp. 615-623.

Powell, B.C.; Kemp, D.J.; Partington, G.A.; Gibbs, P.E.M.; Rogers, G.E.; "Control of feather keratin synthesis by the availability of keratin mRNA."; Biochemical and Biophysical research Communications; vol. 68, No. 4, 1976, pp. 1263-1271.

Powell, B.C.; Rodgers, G.E.; "Cyclic hair-loss and regrowth in the transgenic mice overexpressing and intermediate filament gene."; The EMBO Journal vol. 9, No. 5, 1990, pp. 1485-1493.

Rana, T.M.; et al; "Specific cleavage of a protein by an attached iron chelate."; Journal of the American Chemical Society; vol. 112 (6), 1990, pp. 2457-2458.

Randall, V.A.; "The use of dermal papilla cells in studies of normal and abnormal hair follicle biology."; Dermatologic Clinics; vol. 14, No. 4 1996 pp. 585-594.

Ranford, J.D.; et al; "Matallodrugs. The role of thiolate proteins and metal-thiolate complexes."; Metallothioneins, Conference General Review; 1992, pp. 408-435.

Ranshoff, S.; et al; "Synthesis and characterization of new dioxygen carriers: a reexamination of the fly-over ligand system."; Inorganic Chemistry; vol. 29(16), 1990, pp. 2945-2947.

Raphael, K.A.; et al; "Protein and amino acid composition of hair from mice carrying the naked (N) gene."; Genetic Research, vol. 44, No. 1, 1984, pp. 29-38.

Rappolee, D.A.; et al.; "Wound macrophages express TGF-α and other growth factors in vivo: Analysis by mRNA phenotyping."; Science; vol. 241, 1988, pp. 708-712.

Rau, H.K; Snigula, H.; Struck, A.; Robert, B.; Scheer, H.; Haehnel, W.; "Design, synthesis and properties of synthetic chlorophyll proteins."; European Journal of Biochemistry; vol. 268, 2001, pp. 3284-3295.

Reis, P.J.; "Influence of dietary protein and methionine on the sulphur content and growth rate of wool in the millk fed lambs" Australian Journal of Biological Science; vol. 23, No. 1, 1970, pp. 193-200.

Reis, P.J.; "The growth and composition of wool—III. Variations in the sulphur content of wool."; Australian Journal of Biological Sciences; vol. 18, 1965, pp. 671-687.

Reis, P.J.; "The growth and composition of wool. IV. The differential response of growth and of sulphur content of wool to the level of sulphur containing amino acids given per abomasum" Australian Journal of Biological Science; vol. 20, No. 4, 1967, pp. 809-825.

Reis, P.J.; et al; "The utilization of abomasal supplements of proteins and amino acids by sheep with special reference to wool growth"; Australian Journal of Biological Sciences; vol. 25, 1972, pp. 1057-1071.

Reis, P.J.; et al; "The influence of abomasal and intervenous supplements of sulphur containing amino acids on wool growth rate"; Australian Journal of Biological Sciences; vol. 26, No. 1, 1973, pp. 249-258.

Reis, P.J.; et al; "The nutritional control of the growth and properties of mohair and wool fibers: a comparative review"; Journal of Animal Science; vol. 72, No. 7, 1994, pp. 1899-1907.

Reis, P.J.; Gillespie, J.M.; "Effects of phhenylalanine and the analogues of methionine and phenylalanine on the composition of wool and mouse hair."Australian Journal of Biological Sciences; vol. 38, No. 1, pp. 151-163, 1985.

Reis, P.J.; Tunks, D.A.; Williams, O.B.; Williams, A. J.; "A relationship between sulphur content of wool and wool production by merino sheep."; Australian Journal of Biological Sciences; vol. 20, 1967, pp. 153-163.

Reis, P.J.; Variations in the S content of wool.; Biology Skin Hair Growth, Proceedings Symposium; 1964, pp. 365-375.

Rogers, G.E.; "Some observations on the proteins of the inner root sheath cells of hair follicles." Biochimica et Biophysica Acta; vol. 29, 1958, pp. 33-43.

Rogers, G.E. ; et al; "Keratin protofilaments and ribosomes from hair follicles."; Nature, vol. 205, 1965, pp. 77-78.

Rogers, G.E. et al.; "An approach to the investigation of protein biosynthesis in hair follicles." *Biology of Skin Hair Growth*, Proceedings, 1965, pp. 329-343.

Rogers, G.E.; "Genetic engineering for novel fibres."; Journal of the Textile Institute; vol. 91, part 3, Special Issue, 2000, pp. 24-31.

Rogers, G.E.; "Improvement of wool production through genetic engineering."; Trends in biotechnology (Personnel edition); vol. 8, 1990, pp. 6-11, 32 references.

Rogers, G.E.; "Proteins of the inner-root-sheath cells of hair follicles."; Biochimica et Biophysica Acta; vol. 29, 1958, pp. 33-43.

Rogers, G.E,; "Structural and biochemical features of the hair follicles."; Epidermis; 1964, pp. 179-236.

Rogers, G.E.; "Structure and biochemistry of keratin."; The Biological Basis of Medicine.; vol. 6, 1969, pp. 21-57.

Rogers, G.E.; "Synthesis and cross-linking in the structure and growth of hair keratins." Clinics in Dermatology; vol. 6, No. 4, 1988, pp. 26-31.

Rogers, G.E.; et al; "Protein biosynthesis in hair follicles."; Biology of Skin Hair Growth., Proceedings ; 1965, pp. 329-343.

Rogers, G.E.; et al; "A procedure for the culture of hair follicles as functionally intact organoids."; Clinics in Dermatology; vol. 6, No. 4, 1988. pp. 36-41.

Rogers, G.E.; et al; "A sensitive assay for the enzyme activity in hair follicles and epidermis that catalyzes the peptidyl-arginine-citrulline posttranslational modification." Current Problems Dermatology; vol. 11, 1983, pp. 171-184.

Rogers, G.E.; et al; "Organization and expresson of hair follicle genes."; Journal of Investigative Dermatalogy; vol. 101, 1993, pp. 50 S-55 S.

Rogers, G.E.; et al; "Themes in the molecular structure of hair—discussion." Annals New York Academy Science; vol. 642, 1991, pp. 100-106.

Roop, D.R.; Cheng, C.K.; Titterington, L.; Meyers, C.A.; Stanley, J.R.; Steinert, P.M.; Yuspa, S.H.; "Synthetic peptides corresponding to keratin subunits elicit highly specific antobodies." The Journal of Biological Chemistry; vol. 259, No. 13 1984, pp. 8037-8040.

Ross, S.A.; et al; "Nickel complexes of cysteine- and cystine-containing peptides: Spontaneous formation of disulfide-bridged dimers at neutral pH."; Inorganic Chemistry, vol. 37 (20), 1998, pp. 5358-5363.

Rouse, J.G.; et al; "A review of keratin-based biomaterials for biomedical applications." Materials; vol. 3, 2010, pp. 999-1014.

Rowlands, R.J.; "Periodicity in high-sulphur proteins from wool."; Nature; vol. 246, No. 5434, 1973, pp. 530-531.

Sadova, S. F.; et al; "Grafting of vinyl monomers onto wool keratin in an oxidation-reduction system."; Zh. Vses. Khim. O-va, vol. 12(5), 1967, pp. 596-597.

Sander, G.; et al; "Expresssion of the homeobox gene, Barx2, in wool follicle development."; Journal of Investigative Dermatology; vol. 115, No. 4, 2000, pp. 753-756.

Sauk, J.J. et al; "Reconstitution of cytokeratin filaments in vitro: Further evidence for the role of nonhelical peptides in filament assembly."; The Journal of Cell Biology; vol. 99, 1984, pp. 1590-1597.

Schaller, J.; et al; "Membranes prepared from keratin-polyacrylonitrile graft copolymers." Journal of Applied Polymer Sciences; vol. 25(5), 1980, pp. 783-794.

Schornig, M.; Heumann, R.; Rohrer, H.; "Synthesis of nerve growth factor mRNA in cultures of developing mouse whisker pad, a peripheral target tissue of sensory trigeminal neurons."; The Journal of Cell Biology; vol. 120, No. 6, Mar. 1993, p. 1471-1479.

Schrooyen, P.M.M.; et al; "Biodegrable films from selectively modified feather keratin dispersions."; Polymer Preprints; vol. 39, No. 2, 1998, pp. 160.

Schrooyen, P.M.M.; et al; "Polymer films from chicken feather keratin."; Book of Abstracts, American Chemical Society National Meeting Boston, 1998.

Shah, M.; et al.; "Neutralisation of TGF-$\beta_1$ and TGF-$\beta_2$ or exogenous addition of TGF-$\beta_3$ to cutaneous rat wounds reduces scarring." Journal of Cell Science; vol. 108, 1995, pp. 985-1002.

\* cited by examiner

KERATIN BIOMATERIALS FOR TREATMENT OF ISCHEMIA

RELATED APPLICATIONS

This application claims the benefit under 35 U.S.C. §119(e) of U.S. Provisional Patent Application Ser. No. 61/311,574, filed Mar. 8, 2010, the disclosure of which is incorporated herein by reference in its entirety.

FIELD OF THE INVENTION

The present invention relates to keratin-based biomaterials and the use thereof for methods of treatment for ischemia and/or reperfusion injury.

BACKGROUND

Ischemia is an acute condition associated with an inadequate flow of oxygenated blood to a part of the body, caused by the constriction or blockage of the blood vessels supplying it. This reduction in blood flow can result from the blockage of a vessel by an embolus (blood clot), the blockage of a vessel due to atherosclerosis, etc. The restriction of blood flow quickly causes necrosis in the effected tissues.

SUMMARY

Provided herein are keratin compositions and methods of treating ischemia and/or reperfusion injury (e.g., associated with myocardial infarct, ischemic stroke, brain trauma such as traumatic brain injury, hypothermia, chronic wounds, and burns) in a subject in need thereof (e.g., a human subject) including administering the keratin compositions to the subject in an amount effective to treat the ischemia and/or reperfusion injury.

In some embodiments, the keratin is keratose selected from the group consisting of: α-keratose, γ-keratose, α-kerateine, γ-kerateine, keratin associated proteins (KAP), and combinations thereof.

In some embodiments, the composition comprises (includes), consists of or consists essentially of: (a) from 0.1 to 10 percent by weight of keratin; and (b) from 90 to 99.9 percent by weight of an electrolyte solution; wherein the keratose is solubilized in the electrolyte solution (e.g., normal saline) to form a homogeneous liquid composition having (i) a pH of 7-8; (ii) an osmolarity of 200 to 500 milliosmoles/Liter; and (iii) a viscosity of 2 to 20 centipoise, as determined at a temperature of 37 degrees Celsius in a Brookfield viscometer having a cone and plate geometry with a cone angle of 0.02 radians at a constant frequency of 30 rotations per minute.

In some embodiments, the compositions are administered in combination with a thrombolytic or an anticoagulant.

Compositions including keratin such as keratose and further including a thrombolytic or anticoagulant are also provided.

Further provided is the use of a keratin composition as provided herein for the treatment of ischemia and/or reperfusion injury (e.g., associated with myocardial infarct, ischemic stroke, brain trauma such as traumatic brain injury, hypothermia, chronic wounds, and burns).

DETAILED DESCRIPTION OF THE PREFERRED EMBODIMENTS

Figure 1:
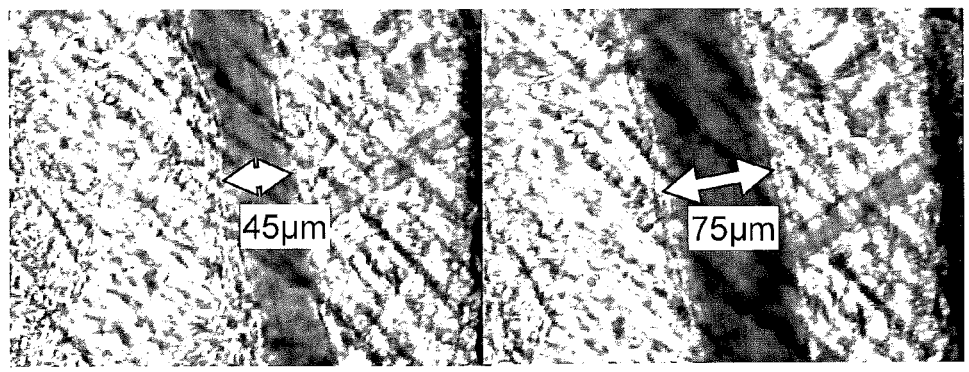
FIG. 1. Dilation of a small diameter arteriole following top-load administration of KRF.

Provided herein according to some embodiments are keratin fluids which are useful to increase and/or restore blood flow and perfusion to ischemic cells and tissues, and the use of these fluids to treat patients in need of such therapy for conditions such as myocardial infarct, stroke, traumatic brain injury (TBI) including mild TBI and other brain trauma, hypothermia, chronic wounds, burns, and other conditions of ischemia.

The disclosures of all cited U.S. patent references are hereby incorporated by reference to the extent they are consistent with the disclosure herein. As used herein in the description of the invention and the appended claims, the singular forms "a," "an" and "the" are intended to include the plural forms as well, unless the context clearly indicates otherwise.

Furthermore, the terms "about" and "approximately" as used herein when referring to a measurable value such as an amount of a compound, dose, time, temperature, and the like, is meant to encompass variations of 20%, 10%, 5%, 1%, 0.5%, or even 0.1% of the specified amount. Also, as used herein, "and/or" refers to and encompasses any and all possible combinations of one or more of the associated listed items, as well as the lack of combinations when interpreted in the alternative ("or").

According to some embodiments, the administration of keratin compositions as described herein increases blood vessel diameter (normal and/or vasoconstricted), along with blood flow, such that a blockage can be overcome. The keratin composition of some embodiments causes significant vasodilation independent of viscosity. In some embodiments, blood vessel diameter is increased by between 10, 15, 20 or 30% and 40, 50, 60 or 70%. In other embodiments, blood vessel diameter is increased by about 2%, about 5%, about 10%, about 15%, 20%, about 25%, about 30%, about 35%, about 40%, about 45%, about 50%, about 55%, about 60%, about 65%, about 70%, about 75%, about 80%, about 85%, about 90%, about 95%, about 100%, about 125%, about 150%, about 175%, about 200%, about 225%, about 250%, about 275%, about 300%, or more, than prior to administration of a keratin composition.

"Ischemia" is a restriction, shortage or blockage in blood supply due to events in the blood vessels such as vessel constriction, blockage by thrombosis or embolism, etc., often with resultant tissue damage and/or dysfunction. A "reperfusion injury" is an injury in which tissue is damaged upon return of blood supply after a period of ischemia.

"Myocardial infarct" or "myocardial infarction," commonly known as a heart attack, is an interruption in blood supply to part of the heart muscle, causing myocardial cell death.

"Stroke" or "cerebrovascular accident" is an interruption in blood supply to part of the brain, often causing brain tissue damage and loss of brain function. "Ischemic stroke" or "cerebral infarction", is caused by a blockage of blood vessels such as thrombosis, embolism, or systemic hypoperfusion (e.g., shock).

Ischemia and/or reperfusion injury may also be a factor in traumatic brain injury (TBI) including mild TBI and other brain trauma, hypothermia (a body temperature below 95 degrees Fahrenheit), chronic wounds, burns, etc. Thus, in some embodiments compositions taught herein are useful in the treatment of these conditions.

In some embodiments, keratin compositions are administered in combination with an anticoagulant and/or a thrombolytic. The administration of two or more compounds "in combination" or "in conjunction" means that the two compounds are administered closely enough in time to have an additive and/or synergistic effect. The two compounds may be administered simultaneously (concurrently) or sequentially. Simultaneous administration may be carried out by mixing the compounds prior to administration, or by administering the compounds at the same point in time but at different anatomic sites or using different routes of administration.

Compositions comprising keratin and further comprising an anticoagulant are provided. Anticoagulants are pharmaceutical agents that decrease the growth of blood clots. Anticoagulants include heparin.

Compositions comprising keratin and further comprising a thrombolytic are provided. Thrombolytics are pharmaceutical agents that break down or reduce the size of blood clots, and include tissue plasminogen activator (tPA) and analogs thereof. Thrombolytics include streptokinase, urokinase, alteplase, reteplase, and tenecteplase. To produce keratin biomaterials as described herein, sub-families of keratin proteins may be isolated, and in some embodiments recombined into a reconstituted composition. "Reconstituted composition" as used herein means a composition comprising different ratios of independently isolated fractions of keratin materials, including, but not limited to, alpha-keratose, acidic alpha-keratose, basic alpha-keratose, gamma-keratose, acidic gamma-keratose, basic gamma-keratose, alpha-kerateine, acidic alpha-kerateine, basic alpha-kerateine, gamma-kerateine, acidic gamma-kerateine, basic gamma-kerateine, KAPs, alpha-keratose monomers, or alpha-kerateine monomers. The composition is created by mixing together the desired proportions of the isolated fractions in solid, liquid, or hydrogel form. In some preferred embodiments, the reconstituted composition is substantially free of KAPs. In other preferred embodiments, the reconstituted composition is substantially free of alpha-keratose monomers and/or alpha kerateine monomers.

In some embodiments, the composition includes from 0.01, 0.1, 0.5, 1, or 2% to 3, 4, 5, 10, 25, 50 or 70% by weight of keratin. Thus, in some embodiments, compositions of the invention comprise about 0.1%, about 0.25%, about 0.5%, about 0.75%, about 1%, about 1.25%, about 1.5%, about 1.75%, about 2%, about 2.25%, about 2.5%, about 2.75%, about 3%, about 3.25%, about 3.5%, about 3.75%, about 4%, about 4.25%, about 4.5%, about 4.75%, about 5%, about 5.25%, about 5.5%, about 5.75%, about 6%, about 6.25%, about 6.5%, about 6.75%, about 7%, about 7.25%, about 7.5%, about 7.75%, about 8%, about 8.25%, about 8.5%, about 8.75%, about 9%, about 9.25%, about 9.5%, about 9.75%, or about 10% by weight of a keratin such as an alpha keratose, an alpha kerateine, keratin associate proteins (KAP), or a combination thereof. For example, compositions of the invention may comprise 0.1%, 0.25%, 0.5%, 0.75%, 1%, 1.25%, 1.5%, 1.75%, 2%, 2.25%, 2.5%, 2.75%, 3%, 3.25%, 3.5%, 3.75%, 4%, 4.25%, 4.5%, 4.75%, 5%, 5.25%, 5.5%, 5.75%, 6%, 6.25%, 6.5%, 6.75%, 7%, 7.25%, 7.5%, 7.75%, 8%, 8.25%, 8.5%, 8.75%, 9%, 9.25%, 9.5%, 9.75%, or 10% by weight of a keratin such as an alpha keratose, an alpha kerateine, keratin associate proteins (KAP), or a combination thereof.

Also, in some embodiments, compositions of the invention comprise about 0.1%, about 0.25%, about 0.5%, about 0.75%, about 1%, about 1.25%, about 1.5%, about 1.75%, about 2%, about 2.25%, about 2.5%, about 2.75%, about 3%, about 3.25%, about 3.5%, about 3.75%, about 4%, about 4.25%, about 4.5%, about 4.75%, about 5%, about 5.25%, about 5.5%, about 5.75%, about 6%, about 6.25%, about 6.5%, about 6.75%, about 7%, about 7.25%, about 7.5%, about 7.75%, about 8%, about 8.25%, about 8.5%, about 8.75%, about 9%, about 9.25%, about 9.5%, about 9.75%, or about 10% by weight an alpha keratose, an alpha kerateine, a gamma keratose, a gamma kerateine, keratin associate proteins (KAP), or a combination thereof. In yet other embodiments, compositions of the invention comprise 0.1%, 0.25%, 0.5%, 0.75%, 1%, 1.25%, 1.5%, 1.75%, 2%, 2.25%, 2.5%, 2.75%, 3%, 3.25%, 3.5%, 3.75%, 4%, 4.25%, 4.5%, 4.75%, 5%, 5.25%, 5.5%, 5.75%, 6%, 6.25%, 6.5%, 6.75%, 7%, 7.25%, 7.5%, 7.75%, 8%, 8.25%, 8.5%, 8.75%, 9%, 9.25%, 9.5%, 9.75%, or about 10% by weight of an alpha keratose, an alpha kerateine, a gamma keratose, a gamma kerateine, keratin associate proteins (KAP), or a combination thereof.

In some embodiments, compositions of the invention include KAP. In alternative embodiments, compositions of the invention are free or substantially free of KAP.

Keratins are a family of proteins found in the hair, skin, and other tissues of vertebrates. Hair is a unique source of human keratins because it is one of the few human tissues that is readily available and inexpensive. Although other sources of keratins are acceptable feedstocks for the present invention, (e.g., wool, fur, horns, hooves, beaks, feathers, scales, and the like), human hair is preferred for use with human subjects because of its biocompatibility. The human hair can be end-cut, as one would typically find in a barber shop or salon.

"Keratin" or "keratin derivative" as used herein refers to any keratin fractionation, derivative, subfamily, etc., or mixtures thereof, alone or in combination with other keratin derivatives or other ingredients, including, but not limited to, alpha keratose, gamma keratose, alpha kerateine, gamma kerateine, meta keratin, keratin intermediate filaments, and combinations thereof, including the acidic and basic constituents thereof unless specified otherwise, along with variations thereof that will be apparent to persons skilled in the art in view of the present disclosure.

"Subjects" are generally human subjects and include, but are not limited to, "patients." The subjects may be male or female and may be of any race or ethnicity, including, but not limited to, Caucasian, African-American, African, Asian, Hispanic, Indian, etc. The subjects may be of any age, including newborn, neonate, infant, child, adolescent, adult, and geriatric.

Subjects also include animal subjects, particularly mammalian subjects such as canines, felines, bovines, caprines, equines, ovines, porcines, rodents (e.g., rats and mice), lagomorphs, non-human primates, etc., for, e.g., veterinary medicine, laboratory research and/or pharmaceutical drug development purposes.

"Treat" refers to any type of treatment that imparts a benefit to a patient, e.g., a patient who is injured or who is afflicted with or at risk for developing a disease (e.g., stroke, myocardial disease, cardiovascular disease, etc.). Treating includes actions taken and actions refrained from being taken for the purpose of improving the condition of the patient (e.g., the relief of one or more symptoms), delay in the onset or progression of the disease, etc. Also, in some embodiments, treating comprises inhibiting, reducing, and/or preventing the disease or symptoms thereof in a subject in need.

In some embodiments, compositions comprising, consisting of or consisting essentially of keratin potentiates the release of strong vasodilators and induces net intravascular transport of water, increasing circulating volume. This results in peripheral vasodilation and increased cardiac contractility (the ability of the cardiac muscle to contract at a given fiber length), which translates into lower cardiac work and better tissue perfusion. Vital signs which may be measured and/or monitored in connection with the treatments described herein include, but are not limited to, mean arterial blood pressure (MAP—average arterial pressure during a cardiac cycle), shock index, base deficit, renal output, kidney function, hematocrit, blood gases, etc., which may be indicative of ischemia and/or reperfusion injury. In some embodiments, the invention provides methods of treating, inhibiting, reducing, and/or preventing the disease or at least one symptom thereof wherein a patient in need wherein said patient exhibits a 5%, 10%, 15%, 20%, 25%, 30%, 35%, 40%, 45%, 50%, 55%, 60%, 65%, 70%, 75%, 80%, 85%, 90%, 95%, or 100% improvement in the disease or symptom thereof as compared to prior to administration of the composition to the patient.

In other embodiments, the invention provides methods of treating, inhibiting, reducing, and/or preventing the disease or at least one symptom thereof wherein a subject in need wherein said patient exhibits improvement in about 1 min, about 2 min, about 5 min, about 10 min, about 15 min, about 30 min, about 60 min, about 120 min, or about 180 min as compared to prior to administration of the composition to the subject.

In other embodiments, the invention provides compositions that increase vasodilation over other fluids used for reperfusion and/or ischemia applications. Such fluids include, but are not limited to Hetastarch and PBS. Thus, in some embodiments, compositions of the invention increase vasodilation about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 125%, about 150%, about 175%, about 200%, about 250%, or about 300% or more than the vasodilation exhibited with other fluids.

In some embodiments, subjects to be treated may have a systolic blood pressure of between 120, 130, 140 or 150 and 180, 200, 250 or 300 mm Hg, and/or a diastolic blood pressure of between 80, 85, 90, 95, or 100 and 120, 125 or 130 mm Hg (hypertension or prehypertension). In some embodiments, subjects to be treated may have a systolic blood pressure of between 80, 90, 100 or 110 and 120, 130 or 140 mm Hg, and/or a diastolic blood pressure of between 40, 50, or 60 and 70, 80 or 90 mm Hg (normal or low blood pressure).

In some embodiments, subjects to be treated may have a resting pulse of from 60, 70, 80, 90, 100, 110 or 120 to 150, 16 or 170 beats per minute, which may indicate tachycardia depending on the subject (normal rate being from 60-100 beats per minute, taking into consideration that women tend to have higher resting pulses than men, and an athlete may have a normal resting pulse of 40 beats per minute). In some embodiments, subjects to be treated may have a resting pulse of from 10, 20, 30 or 40 to 50, 60, 70 or 80 beats per minute, which may indicate normal or a low pulse rate, again, depending of the subject in question.

In some embodiments, subjects to be treated may have a resting respiration rate of from 20, 25, 30 or 35 to 40, 45 or 50 breaths per minute or more (the normal range being usually 15-20 breaths per minute). In some embodiments, subjects may have a resting respiration rate of 15 breaths per minute or less, down to zero breaths per minute in the case of a subject who has become unconscious.

Extracted keratin solutions are known to spontaneously self-assemble at the micron scale (see, e.g., Thomas et al., Int J Biol Macromol 1986; 8:258-64; van de Locht, Melliand Textilberichte 1987; 10:780-6). Self-assembly results in a highly regular structure with reproducible architectures, dimensionality, and porosity. When the keratin is processed correctly, this ability to self-assemble can be preserved and used to create regular architectures on a size scale conducive to molecular infiltration and/or attachment. When keratins are hydrolyzed (e.g., with acids or bases), their molecular weight is reduced, and they lose the ability to self-assemble. Therefore, processing conditions that minimize hydrolysis are preferred.

Soluble keratins can be extracted from human hair fibers by oxidation or reduction using methods known in the art (see, for example, Rouse J G, Van Dyke M E. A review of keratin-based biomaterials for biomedical applications. Materials 2010; 3:999-1014). These methods typically employ a two-step process whereby the crosslinked structure of keratins is broken down by either oxidation or reduction. In these reactions, the disulfide bonds in cystine amino acid residues are cleaved, rendering the keratins soluble. The cuticle is essentially unaffected by this treatment, so the majority of the keratins remain trapped within the cuticle's protective structure. In order to extract these keratins, a second step using a denaturing solution is employed. Alternatively, in the case of reduction reactions, these steps can be combined. Denaturing solutions known in the art include urea, transition metal hydroxides, surfactant solutions, and combinations thereof. Preferred methods use aqueous solutions of tris base (2-Amino-2-(hydroxymethyl)-1,3-propanediol) in concentrations between 0.1 and 1.0 M, and urea solutions between 0.1 and 10M, for oxidation and reduction reactions, respectively.

If one employs an oxidative treatment, the resulting keratins are referred to as "keratoses." If a reductive treatment is used, the resulting keratins are referred to as "kerateines" (See Scheme 1).

Scheme 1.
General representations of (a) oxidation and (b) reduction of disulfide crosslinks in keratin. These reactions cleave the sulfur-sulfur bond in cystine residues, thereby destroying the superstructure and rendering the keratins soluble in the reaction media. The resultant fractions are keratose (a) and kerateine (b).

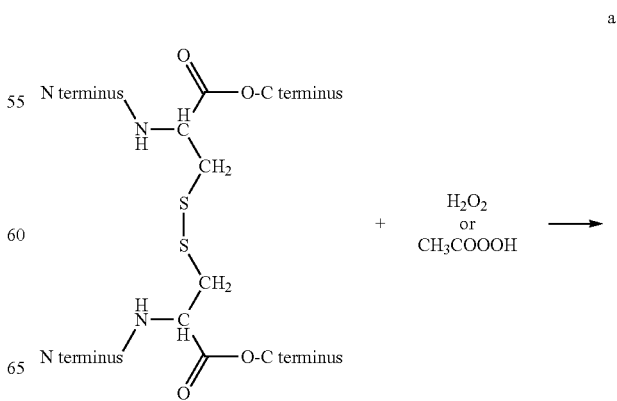

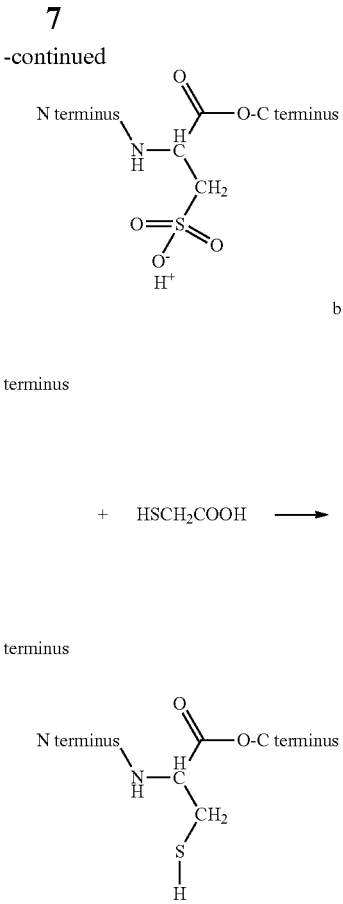

Crude (unfractionated) extracts of keratins, regardless of redox state, can be further refined into matrix (KAP and gamma), alpha, and/or charged (acidic or basic) fractions by a variety of methods such as isoelectric precipitation, dialysis, or high performance liquid chromatography (HPLC), as desired. In a crude extract, the alpha fraction begins to precipitate below pH 6 and is essentially completely precipitated by pH 4.2.

In some embodiments, KAP co-precipitate with the alpha fraction, thereby producing an alpha/KAP mixture. See Rogers et al., "Human Hair Keratin-Associated Proteins (KAPs)," Int'l ref. cytol. 251:209-263 (2006).

High molecular weight keratins, or "alpha keratins," (alpha helical), are thought to originate from the microfibrillar regions of the hair follicle, and monomers of alpha keratins typically range in molecular weight from about 40-85 kiloDaltons. They may also exist as higher-ordered structures, i.e., complexed into multimeric forms with each other or other keratins. Low molecular weight keratins, or "gamma keratins," or keratin-associated proteins (globular), are thought to originate from the matrix regions of the hair follicle, and typically range in molecular weight from about 3-30 kiloDaltons for KAP and 10-15 kiloDaltons for gamma keratins (see Rouse J G, Van Dyke M E. A review of keratin-based biomaterials for biomedical applications. Materials 2010; 3:999-1014).

In some embodiments, the keratin preparations (particularly alpha and/or gamma kerateine and alpha and/or gamma keratose) have an average molecular weight of from about 10, 20, 30, 40 or 50 to 70, 80, 85, 90, 95 or 100 kiloDaltons. Other keratin derivatives, particularly complexed keratins, may have higher average molecular weights, e.g., up to 200 or 300 kiloDaltons.

Even though alpha and gamma keratins possess unique properties, the properties of subfamilies of both alpha and gamma keratins can only be revealed through more sophisticated means of purification and separation. Additional properties that are beneficial emerge and can be optimized upon further separation and purification of crude keratin extracts. Many protein purification techniques are known in the art, and range from the most simplistic, such as fractional precipitation, to the more complex, such as immunoaffinity chromatography. For extensive treatment of this subject, see Scopes R K (editor) Protein Purification: Principles and Practice (3rd ed. Springer, New York 1993); Roe S, Protein Purification Techniques: A Practical Approach (2nd ed. Oxford University Press, New York 2001); Hatti-Kaul R and Mattiasson B, Isomation and Purification of Proteins (Marcel Dekker AG, New York 2003). For example, sub-families of acidic and basic keratin are separable by moving boundary electrophoresis. A preferred method of fractionation is ion exchange chromatography. It was discovered that these fractions possess unique properties, such as their differential effects on blood cell aggregation (see, e.g., U.S. Pat. No. 7,439,012 to Van Dyke).

In some embodiments, the keratin derivative comprises, consists or consists essentially of a particular fraction or subfraction of keratin. The derivative in some embodiments may comprise, consist or consist essentially of at least 10, 20, 30, 40, 50, 60, 70, 80, 90, 95 or 99 percent by weight of said fraction or subfraction (or more).

In some embodiments, the keratin derivative comprises, consists of, or consists essentially of acidic and/or basic, alpha and/or gamma keratose, where the keratose comprises, consists of or consists essentially of at least 10, 20, 30, 40, 50, 60, 70, 80, 90, 95 or 99 percent by weight of acidic and/or basic, alpha and/or gamma keratose (or more).

In some embodiments, the composition comprises from 0.1 to 10 percent by weight of a keratin. In other embodiments, the composition comprises from 90 to 99.9 percent by weight of an electrolyte solution; wherein the keratin is solubilized in the electrolyte solution (e.g., normal saline) to form a homogeneous liquid composition. In further embodiments, the homogenous liquid composition may have any of: N a pH of 6 or 7 to 8 or 9; (ii) an osmolarity of 200 to 500 milliosmoles/Liter; and (iii) a viscosity of 2 to 20 centipoise. In yet further embodiments, the viscosity of said homogenous liquid composition may be determined at a temperature of 37 degrees Celsius in a Brookfield viscometer. In still yet a further embodiment, the viscosity may exhibit a cone and plate geometry with a cone angle of 0.02 radians at a constant frequency of 30 rotations per minute.

Keratose Production. A preferred method for the production of keratoses is by oxidation with hydrogen peroxide, peracetic acid, or performic acid. A most preferred oxidant is peracetic acid. Preferred concentrations range from 1 to 10 weight/volume percent, the most preferred being approximately 2 w/v %. Those skilled in the art will recognize that slight modifications to the concentration can be made to affect varying degrees of oxidation, with concomitant alterations in reaction time, temperature, and liquid to solid ratio. It has also been discussed by Crewther et al. that performic acid offers the advantage of minimal peptide bond cleavage compared to peracetic acid. However, peracetic acid offers the advantages of cost and availability. A preferred oxidation temperature is between 0 and 100 degrees Celsius. A most preferred oxidation temperature is 37° C. A preferred oxidation time is between 0.5 and 24 hours. A most preferred oxidation time is 10 hours. A preferred liquid to solid ratio is from 5 to 100:1.

A most preferred ratio is 20:1. After oxidation, the hair can be rinsed free of residual oxidant using a copious amounts of purified water.

The keratoses may be extracted from the oxidized hair using an aqueous solution of a denaturing agent. Protein denaturants are well known in the art, but preferred solutions include urea, transition metal hydroxides (e.g. sodium and potassium hydroxide), ammonium hydroxide, and tris(hydroxymethyl)aminomethane (Trizma® base). A preferred solution is Trizma base in the concentration range from 0.01 to 1M. A most preferred concentration is 0.1M. Those skilled in the art will recognize that slight modifications to the concentration can be made to effect varying degrees of extraction, with concomitant alterations in reaction time, temperature, and liquid to solid ratio. A preferred extraction temperature is between 0 and 100 degrees Celsius. A most preferred extraction temperature is 37° C. A preferred extraction time is between 0.5 and 24 hours. A most preferred extraction time is 2 hours. A preferred liquid to solid ratio is from 5 to 100:1. A most preferred ratio is 40:1. Additional yield can be achieved with subsequent extractions with dilute solutions of Trizma base or purified water. After extraction, the residual solids can be removed from solution by centrifugation and/or filtration.

Residual denaturing agent may be removed by dialysis against purified water or buffer solution. Concentration of the dialysis retentate may be followed by lyophilization or spray drying, resulting in a dry powder mixture of gamma and alpha keratoses as well as KAP. Alternately, an alpha/KAP mixture may be isolated from the crude extract solution by dropwise addition of acid until the pH of the solution reaches approximately 4.2. Preferred acids include sulfuric, hydrochloric, and acetic. A most preferred acid is concentrated hydrochloric acid. Precipitation of the alpha/KAP fraction begins at around pH 6.0 and continues until approximately 4.2. Fractional precipitation can be utilized to isolate different ranges of protein with different isoelectric properties. Precipitated alpha/KAP can be recovered by centrifugation, filtration, or the like. The alpha/KAP mixture is further purified by re-dissolving the solids in a denaturing solution. The same denaturing solutions as those utilized for extraction can be used. However, a preferred denaturing solution is Trizma base. Ethylene diamine tetraacetic acid (EDTA) can be added to complex and remove trace metals found in hair. A preferred denaturing solution is 100 mM tris base with 20 mM EDTA or DI water with 20 mM EDTA, if desired. If the presence of trace metals is not detrimental to the intended application, the EDTA step may be omitted. The alpha/KAP mixture can be re-precipitated from this solution by dropwise addition of hydrochloric acid to a final pH of 4.2. Isolation of the solid may be done by centrifugation, filtration or the like. This process can be repeated several times to further purify the alpha/KAP mixture, if desired, although significant destruction of amide bonds should be avoided according to some embodiments. In another preferred embodiment, the alpha/KAP fraction can be isolated from gamma-keratose by dialysis. Providing a high nominal low molecular weight cutoff membrane such that the gamma passes through the membrane and the alpha/KAP is retained can effect such separation. Preferred membranes are those having nominal low molecular weight cutoffs of 15,000 to 100,000 Da. Most preferred membranes are those having nominal low molecular weight cutoffs of 30,000 and 100,000 Da.

The gamma keratose fraction can be isolated by addition to a water-miscible non-solvent. Suitable non-solvents include ethanol, methanol, acetone, and the like. A most preferred non-solvent is ethanol. To effect precipitation, the gamma keratose solution can be concentrated by removal of excess water. This can be done using vacuum distillation, falling film evaporation, microfiltration, etc. After concentration, the gamma keratose solution is added dropwise to an excess of cold non-solvent. A most preferred method is to concentrate the gamma keratose solution to approximately 10 weight/volume (w/v) % protein and add it dropwise to an 8-fold excess of cold ethanol. The precipitated gamma keratose can be isolated by centrifugation or filtration and dried. Suitable methods for drying include freeze drying (lyophilization), air drying, vacuum drying, or spray drying. A most preferred method is freeze drying. Alternately, the gamma keratose can be isolated by dialysis against purified water or buffer solution. Preferred membranes for dialysis are those having nominal low molecular weight cutoffs between 1,000 and 5,000 Da. Most preferred membranes for dialysis are those having nominal low molecular weight cutoffs of 3,000 and 5,000 Da. This solution can be concentrated by additional dialysis and reduced to a dry powder by lyophilization or spray drying.

Several different approaches to further purification can be employed to keratose solutions (e.g., crude, alpha or gamma keratose). Care must be taken, however, to choose techniques that lend themselves to keratin's unique solubility characteristics. One of the most simple separation technologies is isoelectric precipitation. Another general method for separating keratins is by chromatography. Several types of chromatography can be employed to fractionate keratin solutions including size exclusion or gel filtration chromatography, affinity chromatography, isoelectric focusing, gel electrophoresis, ion exchange chromatography, and immunoaffinity chromatography. These techniques are well known in the art and are capable of separating compounds, including proteins, by the characteristics of molecular weight, chemical functionality, isoelectric point, charge, or interactions with specific antibodies, and can be used alone or in any combination to affect high degrees of separation and resulting purity.

A preferred purification method is ion exchange (IEx) chromatography. IEx chromatography is particularly suited to protein separation owning to the amphiphilic nature of proteins in general and keratins in particular. Depending on the starting pH of the solution, and the desired fraction slated for retention, either cationic or anionic IEx (CIEx or AIEx, respectively) techniques can be used. For example, at a pH of 7 and above, both gamma and alpha/KAP keratose fractions are soluble and above their isoelectric points. As such, they are anionic and can be bound to an anionic exchange resin. However, if the pH is below approximately 6, the alpha in the alpha/KAP fraction will not bind to the resin and instead passes through a column packed with such resin. A preferred solution for AIEx chromatography is alpha/KAP solution, isolated as described previously, in weak buffer solution at a concentration between 0 and 5 weight/volume %. A preferred concentration is approximately 2 w/v %. It is preferred to keep the ionic strength of said solution initially quite low to facilitate binding to the AIEx column. This is achieved by using a minimal amount of acid to titrate a purified water solution of the keratin to between pH 5.3 and 6. A most preferred pH is 5.3. This solution can be loaded onto an AIEx column such as DEAE-Sepharose or Q-Sepharose, or processed in bulk without the use of a column. The solution that passes through the column can be collected and further processed as described previously to isolate a fraction of alpha powder.

The basic fraction (including KAP) binds readily due to its lower isoelectric point, and can be washed off the column using salting techniques known in the art. A preferred elution medium is sodium chloride solution. A preferred concentration of sodium chloride is between 0.1 and 2M. A most preferred concentration is 2M. The pH of the solution is preferred to be between 6 and 12. A most preferred pH is 11. In order to maintain stable pH during the elution process, a buffer salt can be added. A preferred buffer salt is Trizma base. A preferred concentration of Trizma base is 100 mM. Those skilled in the art will recognize that slight modifications to the salt concentration and pH can be made to affect the elution of keratin fractions with differing properties. It is also possible to use different salt concentrations and pH's in sequence, or employ the use of salt and/or pH gradients to produce different fractions. Regardless of the approach taken, however, the column eluent can be collected and further processed as described previously to isolate purified fractions of alpha-keratose powders.

A complimentary procedure is also feasible using CIEx techniques. Namely, the alpha/KAP solution can be added to a cation exchange resin such as SP Sepharose (strongly cationic) or CM Sepharose (weakly cationic), and the basic (KAP) fraction collected with the pass through. The retained alpha fraction can be isolated by salting as previously described.

Kerateine Production. Similar to the methods described above for extraction and purification of keratoses, kerateines can be produced by reduction of hair fibers with thioglycolic acid or beta-mercaptoethanol. A most preferred reductant is thioglycolic acid (TGA). Preferred concentrations range from 0.1 to 10M, the most preferred being approximately 1.0M or 0.5M. Those skilled in the art will recognize that slight modifications to the concentration can be made to effect varying degrees of reduction, with concomitant alterations in pH, reaction time, temperature, and liquid to solid ratio. A preferred pH is between 9 and 11. A most preferred pH is 10.2. The pH of the reduction solution is altered by addition of base. Preferred bases include transition metal hydroxides and ammonium hydroxide. A most preferred base is sodium hydroxide. The pH adjustment is affected by dropwise addition of a saturated solution of sodium hydroxide in water to the reductant solution. A preferred reduction temperature is between 0 and 100 degrees Celsius. A most preferred reduction temperature is 37° C. A preferred reduction time is between 0.5 and 24 hours. A most preferred reduction time is 12 hours. A preferred liquid to solid ratio is from 5 to 100:1. A most preferred ratio is 20:1. Unlike the previously described oxidation reaction, reduction is carried out at basic pH. That being the case, keratins are highly soluble in the reduction media and are expected to be extracted. The reduction solution may therefore be combined with the subsequent extraction solutions and processed accordingly.

Reduced keratins are not as hydrophilic as their oxidized counterparts. As such, reduced hair fibers will not swell and split open as will oxidized hair, resulting in relatively lower yields. Another factor affecting the kinetics of the reduction/extraction process is the relative solubility of kerateines. The relative solubility rankings in water, from most to least soluble, is gamma-keratose>alpha-keratose>gamma-kerateine>alpha-kerateine. Consequently, extraction yields from reduced hair fibers are not as high. This being the case, subsequent extractions are conducted with additional reductant plus denaturing agent solutions. Typical solutions for subsequent extractions include TGA plus urea, TGA plus Trizma base, or TGA plus sodium hydroxide. After extraction, crude fractions of alpha/KAP and gamma kerateine can be isolated using the procedures described for keratoses. However, precipitates of gamma and alpha/KAP kerateine re-form their cystine crosslinks upon exposure to oxygen. Precipitates should, therefore, preferably be re-dissolved quickly so as to avoid insolubility during the purification stages, or precipitated in the absence of oxygen.

Purification of kerateine solutions can be conducted similar to those described for keratoses. Those skilled in the art will recognize that the chemical nature of kerateines varies from that of keratoses, primarily in the fate of pendant sulfur groups that will alter chemical properties such as isoelectric points. As such, modifications in the conditions for separation techniques such as ion exchange chromatography are needed for optimization.

In some embodiments, the keratin derivative comprises, consists or consists essentially of a particular fraction or subfraction of keratin. The derivative in some embodiments may comprise, consist or consist essentially of at least 80, 90, 95 or 99 percent by weight of said fraction or subfraction (or more).

In some embodiments, the keratin derivative comprises, consists of, or consists essentially of acidic and/or basic, alpha and/or gamma keratose, where the keratose comprises, consists of or consists essentially of at least 80, 90, 95 or 99 percent by weight of acidic and/or basic, alpha and/or gamma keratose (or more).

In some embodiments, the keratin derivative comprises, consists of, or consists essentially of acidic and/or basic, alpha and/or gamma keratose, where the keratose comprises, consists of, or consists essentially of at least 80, 90, 95 or 99 percent by weight of acidic and/or basic, alpha and/or gamma keratose (or more). In other embodiments, the keratin derivative comprises, consists of, or consists essentially of alpha/KAP keratose, where the keratose comprises, consist of, or consists essentially of at least 80, 90, 95 or 99 percent by weight of alpha/KAP keratose (or more).

In some embodiments, the keratin derivative comprises, consists of, or consists essentially of acidic and/or basic, alpha and/or gamma kerateine, where the kerateine comprises, consists of or consists essentially of at least 80, 90, 95 or 99 percent by weight of acidic and/or basic, alpha and/or gamma kerateine (or more). In other embodiments, the keratin derivative comprises, consists of, or consists essentially of alpha/KAP kerateine, where the kerateine comprises, consist of, or consists essentially of at least 80, 90, 95 or 99 percent by weight of alpha/KAP keratose (or more).

The basic alpha keratose is preferably produced by separating basic alpha keratose from a mixture comprising acidic and basic alpha keratose, e.g., by ion exchange chromatography, and optionally the basic alpha keratose has an average molecular weight of from 10 to 100 or 200 kiloDaltons. More preferably, the average molecular weight is from 30 or 40 to 90 or 100 kiloDaltons. Optionally, but in some embodiments preferably, the process further comprises the steps of re-dissolving said basic alpha-keratose in a denaturing and/or buffering solution, optionally in the presence of a chelating agent to complex trace metals, and then re-precipitating the basic alpha keratose from the denaturing solution. It will be appreciated that the composition preferably contains not more than 5, 2, 1, or 0.1 percent by weight of acidic alpha keratose, or less.

The acidic alpha keratose may be produced by a reciprocal of the foregoing technique: that is, by separating and retaining acidic alpha keratose from a mixture of acidic and basic alpha keratose, e.g., by ion exchange chromatography, and optionally the acidic alpha keratose has an average molecular weight of from 10 to 100 or 200 kiloDaltons. More preferably, the average molecular weight is from 30 or 40 to 90 or 100 kiloDaltons. Optionally, but in some embodiments preferably, the process further comprises the steps of re-dissolving said acidic alpha-keratose in a denaturing solution and/or buffering solution, optionally in the presence of a chelating agent to complex trace metals, and then re-precipitating the basic alpha keratose from the denaturing solution. It will be appreciated that the composition preferably contains not more than 5, 2, 1, or 0.1 percent by weight of basic alpha keratose, or less.

Basic and acidic fractions of other keratoses (e.g., KAP and gamma keratose) can be prepared in like manner as described above for basic and acidic alpha keratose.

Basic alpha kerateine is preferably produced by separating basic alpha kerateine from a mixture of acidic and basic alpha kerateine, e.g., by ion exchange chromatography, and optionally the basic alpha kerateine has an average molecular weight of from 10 to 100 or 200 kiloDaltons. More preferably, the average molecular weight is from 30 or 40 to 90 or 100 kiloDaltons. Optionally, but preferably, the process further includes the steps of re-dissolving said basic alpha-kerateine in a denaturing and/or buffering solution, optionally in the presence of a chelating agent to complex trace metals, and then re-precipitating the basic alpha kerateine from the denaturing solution. It will be appreciated by those of skill in the art that the composition preferably contains not more than 5, 2, 1, or 0.1 percent by weight of acidic alpha kerateine, or less.

The acidic alpha kerateine may be produced by a reciprocal of the foregoing technique; that is, by separating and retaining acidic alpha kerateine from a mixture of acidic and basic alpha kerateine, e.g., by ion exchange chromatography, and optionally the acidic alpha kerateine has an average molecular weight of from 5 or 10 to 100 or 200 kiloDaltons. Optionally, but preferably, the process further comprises the steps of re-dissolving said acidic alpha-kerateine in a denaturing and/or buffering solution), optionally in the presence of a chelating agent to complex trace metals, and then re-precipitating the basic alpha kerateine from the denaturing solution. It will be appreciated that the composition preferably contains not more than 5, 2, 1, or 0.1 percent by weight of basic alpha kerateine, or less.

Basic and acidic fractions of other kerateines (e.g., KAP and gamma kerateine) can be prepared in like manner as described above for basic and acidic alpha kerateine. Gamma keratins are typically precipitated in a non-solvent such as ethanol.

As used herein, "acidic" keratins are those keratins that are protonated at a predetermined pH such that they carry a net positive charge; "basic" keratins are those keratins that are de-protonated at a predetermined pH such that they carry a net negative charge. The keratin associated proteins (KAP) as used herein carry a negative charge at the predetermined pH and bind to an anionic exchange resin, and thus in some embodiments is included in the basic keratin fractions taught herein. In some embodiments, the predetermined pH is between 5 and 7. In some embodiments, the pH is 6. For example, in some embodiments, keratose or kerateine is separated into acidic and basic fractions (e.g., by ion exchange chromatography) performed at a solution pH of 6, with the resulting acidic fraction including those keratins having a net positive charge at pH 6, and the basic fraction including those keratins having a net negative charge at pH 6. Likewise, for separation at a predetermined pH of 5.3, the acidic fraction will include those keratins having a net positive charge at pH 5.3 and the basic fraction will include those keratins having a net negative charge at pH 5.3.

Those skilled in the art will recognize that the predetermined pH is selected to effect the best separation between acidic and basic proteins based upon their isoelectric points (see, e.g., Table 1), though solubility at that pH should also be considered. When the pH of the solution is between the iso- electric point of these acidic and basic keratin fractions, basic keratin proteins will be de-protonated to have a net negative charge and bind to an anionic media (e.g., DEAE-Sepharose or Q-Sepharose (anion exchange)), while the acidic proteins will be protonated to have a net positive charge and pass through the column, thereby effecting separation.

Residual reductant and denaturing agents can be removed from solution by dialysis. Typical dialysis conditions are 1 to 2% solution of kerateines dialyzed against purified water. Those skilled in the art will recognize that other methods exist for the removal of low molecular weight contaminants in addition to dialysis (e.g. microfiltration, chromatography, and the like). The use of Trizma base is only required for initial solubilization of the kerateines. Once dissolved, the kerateines are stable in solution without the denaturing agent for finite periods. Therefore, the denaturing agent can be removed without the resultant precipitation of kerateines. Regardless of the fractionation/purification process, the resulting kerateines can be concentrated and lyophilized, similar to keratoses.

The higher the percentage of alpha keratose or alpha kerateine in the composition leads to decreased hydrolytic susceptibility. Conversely, lowering the percentage of alpha keratose or alpha kerateine in the composition leads to increased hydrolytic susceptibility.

Thus, in some embodiments, reconstituted compositions of the invention comprise about 0.1%, about 0.25%, about 0.5%, about 0.75%, about 1%, about 1.25%, about 1.5%, about 1.75%, about 2%, about 2.25%, about 2.5%, about 2.75%, about 3%, about 3.25%, about 3.5%, about 3.75%, about 4%, about 4.25%, about 4.5%, about 4.75%, about 5%, about 5.25%, about 5.5%, about 5.75%, about 6%, about 6.25%, about 6.5%, about 6.75%, about 7%, about 7.25%, about 7.5%, about 7.75%, about 8%, about 8.25%, about 8.5%, about 8.75%, about 9%, about 9.25%, about 9.5%, about 9.75%, or about 10% by weight alpha keratose or alpha kerateine. In yet other embodiments, reconstituted compositions of the invention comprise 0.1%, 0.25%, 0.5%, 0.75%, 1%, 1.25%, 1.5%, 1.75%, 2%, 2.25%, 2.5%, 2.75%, 3%, 3.25%, 3.5%, 3.75%, 4%, 4.25%, 4.5%, 4.75%, 5%, 5.25%, 5.5%, 5.75%, 6%, 6.25%, 6.5%, 6.75%, 7%, 7.25%, 7.5%, 7.75%, 8%, 8.25%, 8.5%, 8.75%, 9%, 9.25%, 9.5%, 9.75%, or 10% by weight alpha keratose or alpha kerateine.

Also, in some embodiments, reconstituted compositions of the invention comprise about 0.1%, about 0.25%, about 0.5%, about 0.75%, about 1%, about 1.25%, about 1.5%, about 1.75%, about 2%, about 2.25%, about 2.5%, about 2.75%, about 3%, about 3.25%, about 3.5%, about 3.75%, about 4%, about 4.25%, about 4.5%, about 4.75%, about 5%, about 5.25%, about 5.5%, about 5.75%, about 6%, about 6.25%, about 6.5%, about 6.75%, about 7%, about 7.25%, about 7.5%, about 7.75%, about 8%, about 8.25%, about 8.5%, about 8.75%, about 9%, about 9.25%, about 9.5%, about 9.75%, or about 10% by weight gamma keratose or gamma kerateine. In yet other embodiments, reconstituted compositions of the invention comprise 0.1%, 0.25%, 0.5%, 0.75%, 1%, 1.25%, 1.5%, 1.75%, 2%, 2.25%, 2.5%, 2.75%, 3%, 3.25%, 3.5%, 3.75%, 4%, 4.25%, 4.5%, 4.75%, 5%, 5.25%, 5.5%, 5.75%, 6%, 6.25%, 6.5%, 6.75%, 7%, 7.25%, 7.5%, 7.75%, 8%, 8.25%, 8.5%, 8.75%, 9%, 9.25%, 9.5%, 9.75%, or about 10% by weight gamma keratose or gamma kerateine.

Further discussion of keratin preparations are found in U.S. Patent Application Publication 2009/0004242 (Van Dyke), which is incorporated by reference herein.

These sub-fractions of keratin have demonstrated interesting characteristics such as an ability to rapidly cause dilation of blood vessels, including collapsed blood vessels, and either increase circulation or restore it, respectively. Using the different fractions of keratoses as described above, either alone or in combination, the fluid properties and therapeutic effects of the keratose solution can be controlled. Unique features of this system include:

An ability to re-combine keratin fractions into reconstituted keratins that have controllable physical properties An ability to tailor physical and bio-compatibility properties to the cardiovascular system An ability to cause dilation of blood vessels upon intravenous administration of a keratose fluid An ability to restore and/or improve blood flow and tissue perfusion with a keratose fluid An ability to treat patients with ischemia-related injuries The vasodilation effect of some keratin fractions coupled with the material properties of the keratin fractions are useful for ischemia reperfusion treatment. The keratin fractions can be modified by varying the percent concentrations of the various fractions and/or by changing extraction processes (i.e. using a 30 kDa MWCO membrane versus a 100 kDa MWCO membrane and/or by column separating KAP from alpha fractions).

Keratose fluid formation is accomplished simply by rehydrating sterile keratose powder with saline or other isotonic solution (e.g. Ringer's lactate) under aseptic conditions. Different sub-fractions of keratose can be used to achieve the desired characteristics of physical properties, bio- and blood-compatibility, and vasodilatory effect. The product can take the form of a ready-to-inject sterile fluid, or to increase shelf life, sterile, lyophilized keratose powder packaged in a container to which isotonic solution can be added. Alternatively, salts to achieve osmotic and pH balance can be added to the powdered keratose and water added. The added liquid can be sterile and added aseptically, or a sterile filtering apparatus can be added to the keratose powder packaging such that the liquid is sterile filtered as it is being added.

Formulations. Dry powders may be formed of keratin preparations described above in accordance with known techniques such as freeze drying (lyophilization). In some embodiments, hydrogel compositions of the invention may be produced by mixing such a dry powder composition form with an aqueous solution to produce a composition having an electrolyte solution with a keratin solubilized therein. The mixing step can be carried out at any suitable temperature, typically room temperature, and can be carried out by any suitable technique such as stirring, shaking, agitation, etc. The salts and other constituent ingredients of the electrolyte solution (e.g., all ingredients except the keratin derivative and the water) may be contained entirely in the dry powder, entirely within the aqueous composition, or may be distributed between the dry powder and the aqueous composition. For example, in some embodiments, at least a portion of the constituents of the electrolyte solution is contained in the dry powder.

In some embodiments, the compositions are sterile. In some embodiments, keratin solutions are sterile filtered and processed aseptically, or terminally sterilized using ethylene oxide, e-beam, gamma, or other low temperature method (i.e. <50° C.).

The keratin composition may be provided as a kit of sterile dry powder in one container and sterile aqueous solution in a separate container for mixing just prior to use. The composition preferably has a shelf life of at least 4 or 6 months (up to 2 or 3 years or more) at room temperature, prior to substantial loss of viscosity (e.g., more than 10 or 20 percent) and/or structural integrity of the keratin gel or hydrogel.

The composition may be provided in a precursor solution aseptically packaged in a suitable container. For example, a gel precursor solution can be provided in a glass ampule ready to use directly or after dilution by the user. In the case of kerateine compositions, which can re-crosslink in the presence of oxygen in air, a sterile precursor solution in a sealed ampule under an inert atmosphere (e.g. nitrogen) can be provided. A user would simply break open the ampule, mix in a compound of interest and use the solution directly or after dilution for producing the gel containing the compounds of interest dispersed therein.

In some embodiments, keratin biomaterial compositions can be formulated for a injection or as a surface treatment (e.g., for burn wounds). Formulations of the invention include those for parenteral administration (e.g., subcutaneous, intramuscular, intradermal, intravenous, intra-arterial, intraperitoneal injection) or implantation. In one embodiment, administration is carried out intravascularly, either by simple injection, or by injection through a catheter positioned in a suitable blood vessel, such as a renal artery.

In some embodiments, compounds of interest are administered in a therapeutically effective amount. The therapeutically effective dosage can be determined in accordance with procedures known to those skilled in the art.

Embodiments of the present invention are further detailed in the following non-limiting examples.

EXAMPLES

Example 1

Keratose as a hyperviscous hyperosmotic compound potentiates the release of strong vasodilators and induces net intravascular transport of water, increasing circulating volume. This results in peripheral vasodilation and increased cardiac contractility which translates into lower cardiac work and better tissue perfusion. The null hypothesis was tested that a Keratose resuscitation fluid (KRF) would not induce more arteriolar vasodilation than a current plasma expander, Hetastarch (HS).

METHODS: Keratose Resuscitation Fluid (KRF) was prepared as a mixture of acidic+basic alpha keratose that had been dialyzed against a 30K nominal low molecular weight cutoff membrane. It was provided at about 5 wt. % in normal saline, pH 7.4. A defined topload volume of resuscitation fluid (2.25 ml/100 g) was infused into euvolemic (normal blood volume) rats. Eleven rats received Keratose Resuscitation Fluid (KRF; matched to whole blood viscosity; ca. 5 wt. %), eleven rats received Hetastarch 6% in 0.9% Sodium Chloride Solution (Hextend) and a control group of seven rats received Phosphate Buffered Saline (PBS). A cremaster muscle microvascular preparation was used to measure changes in diameter of arterioles 20 µm to 65 µm in size. Diameters were measured before infusion and at five-minute intervals up to thirty minutes after infusion.

Figure 2:
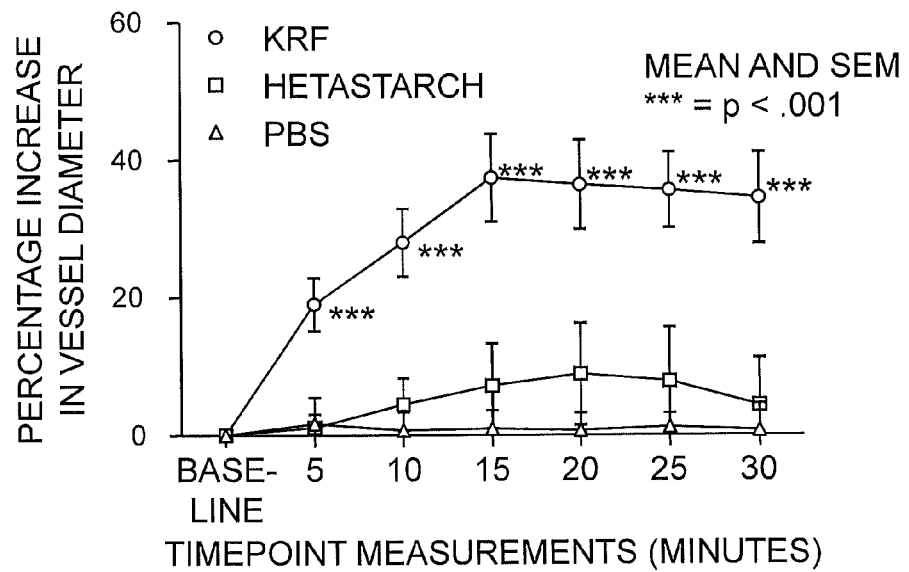
FIG. 2. Microvessel diameters measured in the cremaster muscle following top-load of fluid.

RESULTS: Analysis of variance showed significant differences ($p<0.05$) between the three treatment groups at all time-points (FIG. 2). Bonferroni's multiple comparison tests showed that KRF induced greater vasodilation than PBS or Hetastarch. Hetastarch vasodilatiloty effects were not statistically different than those obtained with PBS.

DISCUSSION: Toploaded KRF induced significant vasodilation in the cremaster microvasculature (FIG. 1) compared to equivalent volumes of Hetastarch or PBS. KRF induced significant vasodilation in muscle microvasculature compared to HS or PBS.

Example 2

Crude keratose solution was further processed to separate it into alpha and KAP fractions. This was accomplished by removing the keratose (alpha/KAP) from dialysis (100K Da NLMWCO), titrating the solution to pH 6.0, and loading the sample onto a glass column containing Q Sepharose anion exchange resin. The resin was used according to the manufacturer's instructions and was conditioned with three volumes of 10 mM tris at pH 6.0. After loading, the sample, the column was rinsed with an additional three volumes of 10 mM tris buffer. The flow through and rinse solutions, representing the alpha fraction, were collected, dialyzed at 30 KDa NLMWCO, and processed to a dry powder. The sample bound to the resin, representing the KAP fraction was washed off with three volumes of 100 mM tris at pH 8.0+2M sodium chloride. This solution was dialyzed at 3 KDa NLMWCO and further processed to a dry powder as previously described. A KAP-containing fluid was prepared by dissolving 20% sterile protein in sterile phosphate buffered saline.

The animal protocol was approved by the Wake Forest University School of Medicine institutional animal care and use committee. Male Sprague-Dawley rats (S-D)(Charles River Laboratories International Inc, Wilmington, Mass.) weighting 95-157 g were studied. All rats were housed in a room with a controlled temperature (20 to 22° C.) and a twelve-hour light-dark cycle, with tap water and rodent chow provided ad libitum. The rats were anesthetized with urethane diluted in 0.9% sodium chloride solution and injected intraperitoneally at a dose of 1 gram per kilogram of body weight or until adequate anesthesia was achieved. Subjects were positioned on the surgery table and the proximal trachea was isolated. A small incision was made between tracheal cartilage rings and a polyethylene tube (PE205) was inserted into the trachea to ensure sufficient and adequate airflow throughout the experiment. The incision was then extended laterally towards the right clavicle until the jugular vein was isolated. A saline-filled catheter was inserted into the jugular vein and secured for later infusion of treatments into the venous bloodstream.

The subjects were repositioned and an incision was made through the lateral aspect of the scrotum for cremaster muscle isolation. The fascia overlying the cremaster muscle was resected and the muscle incised through the midline until its inner contents were exposed. The spermatic chord and its components were ligated and resected. The muscle was completely isolated from other tissues and spread over a glass pedestal, secured with 6-0 silk sutures and a glass cover slip was placed over it for efficient transillumination and to maintain physiologic tissue $PO_2$.

Rats were transferred to a compound microscope (Olympus BH W1, Japan) equipped for videomicroscopy with fiber optic illumination (Fiber-Lite Model 190, Dolan-Jenner Industries, Inc, Woburn, Mass.). Under 40× objective (Nikon, Japan; n.a.=0.5), A2 and A3 arterioles with clearly defined walls, 20 μm to 65 μm in diameter, were selected for study. Microvascular dimensions were measured from video images (MTI CCD-72T, Michigan City, Ind.).

Subjects were allowed to stabilize for one hour after preparation for the vasculature to recover from any transient changes associated with the surgical preparation. A topload-model was employed using a defined volume of fluid (2.25 ml/100 g), which was infused intravenously to the rats in a euvolemic state. This volume represented an increase in blood volume of approximately 33%. The fluids were warmed to body temperature prior to injection and infused through the jugular catheter over a period of two minutes.

Figure 3:
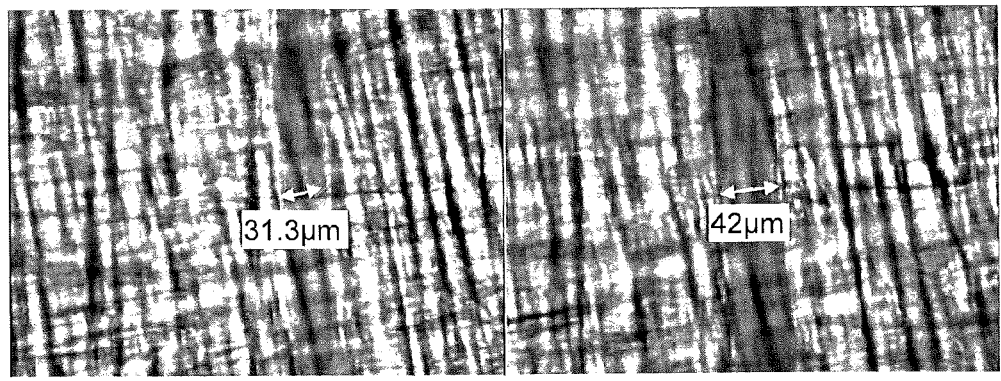
FIG. 3. Arteriole diameter before (left) and 20 minutes after (right) administration of 20% KAP-containing fluid in a rat.

Arteriolar diameter was measured prior to infusion and at five-minute intervals up to thirty minutes after infusion. As shown in FIG. 3, the vessel diameter increased from 31.3 μm to 42 μm (about 34%)

The foregoing is illustrative of the present invention, and is not to be construed as limiting thereof. The invention is defined by the following claims, with equivalents of the claims to be included therein.

That which is claimed is:

1. A method of treating ischemia or reperfusion injury in a subject in need thereof, said method comprising administering a composition comprising a keratin to said subject in an amount effective to treat said ischemia or reperfusion injury, wherein said keratin is a combination of α-keratose and keratin associated proteins (KAP).

2. The method of claim 1, wherein said α-keratose has an average molecular weight of at least 30 kiloDaltons.

3. The method of claim 1, wherein said composition comprises from 1 to 10% by weight of said keratin.

4. The method of claim 1, wherein said keratin is from 3 to 5 percent by weight of said composition.

5. The method of claim 1, wherein said composition consists essentially of:
    (a) from 1 to 10 percent by weight of said keratin; and
    (b) from 90 to 99 percent by weight of an electrolyte solution;
    wherein said keratin is solubilized in said electrolyte solution to form a homogeneous liquid composition having
    (i) a pH of 7-8;
    (ii) an osmolarity of 200 to 500 milliosmoles/Liter; and
    (iii) a viscosity of 2 to 20 centipoise, as determined at a temperature of 37 degrees Celsius in a Brookfield viscometer having a cone and plate geometry with a cone angle of 0.02 radians at a constant frequency of 30 rotations per minute.

6. The method of claim 5, wherein said electrolyte solution is normal saline.

7. The method of claim 5, wherein said keratin is from 3 to 5 percent by weight of said composition.

8. The method of claim 1, wherein said composition is administered in combination with a thrombolytic or an anticoagulant.

9. The method of claim 8, wherein said composition is administered in combination with a thrombolytic.

10. The method of claim 9, wherein said thrombolytic is selected from the group consisting of: streptokinase, urokinase, alteplase, reteplase, and tenecteplase.

11. The method of claim 8, wherein said composition is administered in combination with an anticoagulant.

12. The method of claim 11, wherein said anticoagulant comprises heparin.

13. The method of claim 11, wherein said composition comprising a keratin further comprises said anticoagulant.

14. The method of claim 8, wherein said composition comprising a keratin further comprises said thrombolytic.

15. The method of claim 1, wherein said ischemia or reperfusion injury is myocardial infarction, ischemic stroke, ischemia or reperfusion injury associated with brain trauma, ischemia or reperfusion injury associated with hypothermia, ischemia or reperfusion injury associated with chronic wounds, or ischemia or reperfusion injury associated with burns.

16. The method of claim 1, wherein said ischemia or reperfusion injury is myocardial infarction, ischemic stroke, ischemia or reperfusion injury associated with brain trauma, or ischemia or reperfusion injury associated with hypothermia.

17. The method of claim 1, wherein said ischemia or reperfusion injury is myocardial infarction.

18. The method of claim 1, wherein said ischemia or reperfusion injury is ischemic stroke.

19. The method of claim 1, wherein said ischemia or reperfusion injury is ischemia or reperfusion injury associated with brain trauma.

20. The method of claim 19, wherein said brain trauma is traumatic brain injury (TBI).

21. The method of claim 1, wherein said ischemia or reperfusion injury is ischemia or reperfusion injury associated with hypothermia.

22. The method of claim 1, wherein said composition is formulated for parenteral administration.

23. A method of treating ischemia or reperfusion injury in a subject in need thereof, said method comprising administering a composition comprising a keratin to said subject,
wherein said keratin is combination of α-keratose and keratin associated proteins (KAP), and
wherein said composition is administered in an amount effective to increase arteriolar diameter by 15 to 50%.

24. The method of claim 23, wherein said composition comprises from 1 to 10% by weight of said keratin.

25. The method of claim 23, wherein said keratin is from 3 to 5 percent by weight of said composition.

26. The method of claim 23, wherein said composition is administered in combination with a thrombolytic or an anticoagulant.

27. The method of claim 23, wherein said ischemia or reperfusion injury is myocardial infarction, ischemic stroke, ischemia or reperfusion injury associated with brain trauma, or ischemia or reperfusion injury associated with hypothermia.

28. The method of claim 23, wherein said composition is formulated for parenteral administration.

* * * * *

UNITED STATES PATENT AND TRADEMARK OFFICE
CERTIFICATE OF CORRECTION

PATENT NO.        : 8,545,893 B2                                    Page 1 of 1
APPLICATION NO.   : 13/043062
DATED             : October 1, 2013
INVENTOR(S)       : Van Dyke et al.

It is certified that error appears in the above-identified patent and that said Letters Patent is hereby corrected as shown below:

In the Claims:
Column 19, Claim 23, Line 18: Correct "said keratin is combination of"
                              to read -- said keratin is a combination of --

Signed and Sealed this
Thirtieth Day of September, 2014

Michelle K. Lee
*Deputy Director of the United States Patent and Trademark Office*